(12) United States Patent
Mcfann et al.

(10) Patent No.: US 6,371,928 B1
(45) Date of Patent: Apr. 16, 2002

(54) GUIDEWIRE FOR POSITIONING A CATHETER AGAINST A LUMEN WALL

(75) Inventors: Timothy B. Mcfann, Redwood City; Kathy M. Mah, Mountain View; James D. Passafaro, Los Gatos; Roger W. Perkins, San Jose; Joan Huynh, San Jose; Greg R. Patterson, Pleasanton; Ronald G. Williams, Menlo Park; David J. Kupiecki, San Francisco, all of CA (US)

(73) Assignee: Prolifix Medical, Inc., Sunnyvale, CA (US)

( * ) Notice: Subject to any disclaimer, the term of this patent is extended or adjusted under 35 U.S.C. 154(b) by 0 days.

(21) Appl. No.: 09/417,228

(22) Filed: Oct. 13, 1999

Related U.S. Application Data

(63) Continuation-in-part of application No. 09/389,772, filed on Sep. 3, 1999, which is a continuation-in-part of application No. 09/289,850, filed on Apr. 12, 1999, which is a continuation-in-part of application No. 08/290,510, filed on Apr. 12, 1999, now Pat. No. 6,139,557, which is a continuation-in-part of application No. 08/966,001, filed on Nov. 7, 1997, now Pat. No. 6,156,046.

(60) Provisional application No. 60/103,447, filed on Oct. 7, 1998, provisional application No. 60/099,079, filed on Sep. 4, 1998, now Pat. No. 6,139,557, provisional application No. 60/081,614, filed on Apr. 13, 1998, and provisional application No. 60/081,631, filed on Apr. 13, 1998.

(51) Int. Cl.$^7$ ............................ A61B 5/00; A61M 25/00
(52) U.S. Cl. .................................. 600/585; 600/434
(58) Field of Search ............................ 600/433, 434, 600/435, 585; 604/22, 280; 606/159

(56) References Cited

U.S. PATENT DOCUMENTS

| | | | |
|---|---|---|---|
| 4,706,671 A | 11/1987 | Weinrib | 606/159 |
| 4,732,154 A | 3/1988 | Shiber | 128/305 |
| 4,745,919 A | 5/1988 | Bundy et al. | 604/22 |
| 4,834,724 A * | 5/1989 | Geiss et al. | 604/280 |
| 4,890,611 A | 1/1990 | Monfort et al. | 606/159 |
| 4,909,781 A | 3/1990 | Husted | 604/22 |
| 4,950,277 A | 8/1990 | Farr | 606/159 |
| 4,979,939 A | 12/1990 | Shiber | 606/159 |
| 5,007,896 A | 4/1991 | Shiber | 604/22 |
| 5,011,488 A | 4/1991 | Ginsburg | 606/159 |
| 5,030,201 A | 7/1991 | Palestrant | 604/22 |
| 5,047,040 A | 9/1991 | Simpson et al. | 606/159 |
| 5,054,501 A | 10/1991 | Chuttani et al. | 600/585 |
| 5,078,722 A | 1/1992 | Stevens | 606/159 |
| 5,078,723 A | 1/1992 | Dance et al. | 606/159 |
| 5,100,423 A | 3/1992 | Fearnot | 606/159 |
| 5,116,352 A | 5/1992 | Schnepp-Pesch et al. | 606/171 |
| 5,135,531 A | 8/1992 | Shiber | 606/159 |
| 5,143,085 A | 9/1992 | Wilson | 600/585 |
| 5,158,564 A | 10/1992 | Schnepp-Pesch et al. | 606/159 |
| 5,195,954 A | 3/1993 | Schnepp-Pesch et al. | 604/22 |

(List continued on next page.)

FOREIGN PATENT DOCUMENTS

| | | |
|---|---|---|
| EP | 0448859 | 10/1991 |
| EP | 0254414 | 8/1992 |
| EP | 0501772 | 9/1992 |

(List continued on next page.)

Primary Examiner—John P. Lacyk
Assistant Examiner—Charles Marmor II
(74) Attorney, Agent, or Firm—Townsend and Townsend and Crew LLP

(57) ABSTRACT

The present invention relates to a guidewire having a shaped three dimensional guide section. In the preferred embodiment the guide section is helical, and exerts an outward radial force on a lumen the guidewire is constrained in. The outward radial force can be measured or calculated according to methods of the present invention. Also described is a system comprising a guidewire and catheter where the force the catheter exerts on a body lumen can also be calculated. Apparatus and methods of making the guidewire are also disclosed, as well as alternative embodiments of the guidewire.

48 Claims, 20 Drawing Sheets

U.S. PATENT DOCUMENTS

| | | | | |
|---|---|---|---|---|
| 5,224,945 | A | 7/1993 | Pannek Jr. | 606/159 |
| 5,251,640 | A | 10/1993 | Osborne | 600/585 |
| 5,269,751 | A | 12/1993 | Kaliman et al. | 604/22 |
| 5,306,244 | A | 4/1994 | Shiber | 604/53 |
| 5,306,252 | A | 4/1994 | Yutori et al. | 604/164 |
| 5,314,407 | A | 5/1994 | Auth et al. | 604/22 |
| 5,314,438 | A | 5/1994 | Shturman | 606/159 |
| 5,318,576 | A | 6/1994 | Plassche, Jr. et al. | 606/159 |
| 5,320,634 | A | 6/1994 | Vigil et al. | 606/159 |
| 5,334,211 | A | 8/1994 | Shiber | 606/159 |
| 5,356,418 | A | 10/1994 | Shturman | 606/159 |
| 5,360,432 | A | 11/1994 | Shturman | 606/159 |
| 5,402,799 | A | 4/1995 | Colon et al. | 600/585 |
| 5,403,334 | A | 4/1995 | Evans et al. | 606/159 |
| 5,409,015 | A | 4/1995 | Palermo | 600/585 |
| 5,417,703 | A | 5/1995 | Brown et al. | 606/159 |
| 5,443,443 | A | 8/1995 | Shiber | 604/22 |
| 5,490,859 | A | 2/1996 | Mische et al. | 606/159 |
| 5,496,277 | A | 3/1996 | Termin et al. | 604/104 |
| 5,497,782 | A | 3/1996 | Fugoso | 600/585 |
| 5,501,694 | A | 3/1996 | Ressemann et al | 606/159 |
| 5,514,115 | A | 5/1996 | Frantzen et al | 604/281 |
| 5,522,875 | A | 6/1996 | Gates et al. | 607/127 |
| 5,527,326 | A | 6/1996 | Hermann et al. | 606/159 |
| 5,540,707 | A | 7/1996 | Ressemann et al. | 606/159 |
| 5,556,408 | A | 9/1996 | Farhat | 606/180 |
| 5,569,277 | A | 10/1996 | Evans et al. | 606/159 |
| 5,571,122 | A | 11/1996 | Kelley et al. | 606/159 |
| 5,584,843 | A | 12/1996 | Wulfman et al. | 606/159 |
| 5,596,996 | A | 1/1997 | Johanson et al. | 600/585 |
| 5,616,149 | A | 4/1997 | Barath | 606/159 |
| 5,620,451 | A | 4/1997 | Rosborough | 606/108 |
| 5,622,188 | A | 4/1997 | Plaia et al. | 606/194 |
| 5,643,298 | A | 7/1997 | Nordgren et al. | 606/159 |
| 5,830,156 | A * | 11/1998 | Ali | 600/585 |
| 5,904,657 | A * | 5/1999 | Unsworth et al. | 600/585 |

FOREIGN PATENT DOCUMENTS

| | | |
|---|---|---|
| EP | 0360791 | 8/1994 |
| EP | 0337918 | 11/1994 |
| EP | 0421457 | 1/1995 |
| EP | 0379786 | 3/1995 |
| EP | 0680730 | 11/1995 |
| EP | 0442137 | 2/1996 |
| EP | 0963764 | 12/1999 |
| WO | WO 82/04388 | 12/1982 |
| WO | WO 89/00835 | 2/1989 |
| WO | WO 94/04081 | 3/1994 |
| WO | WO 94/10919 | 5/1994 |
| WO | WO 95/27443 | 10/1995 |
| WO | WO 96/39084 | 12/1996 |
| WO | WO 98/35717 | 8/1998 |
| WO | WO 99/23958 | 5/1999 |

* cited by examiner

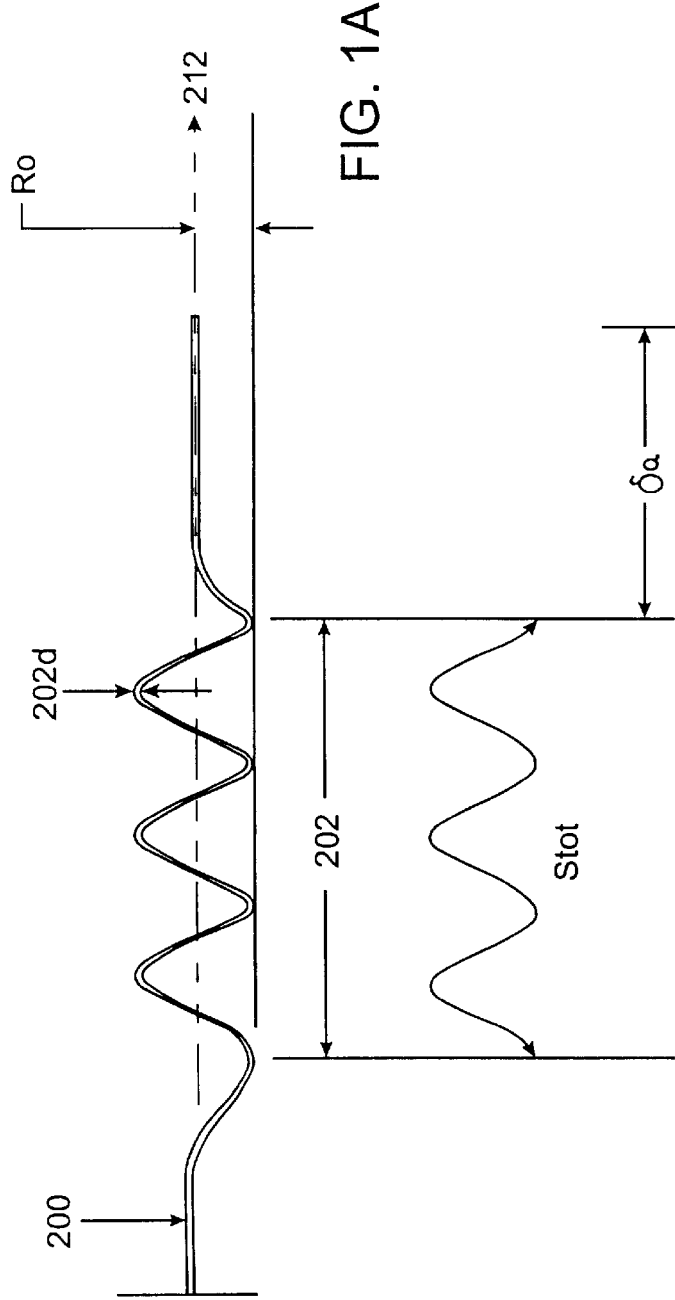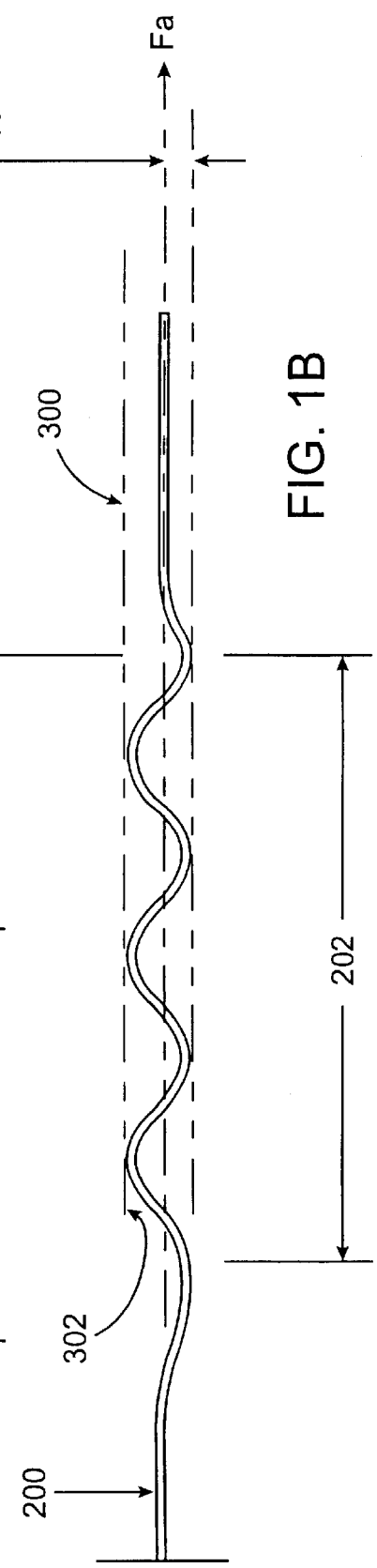

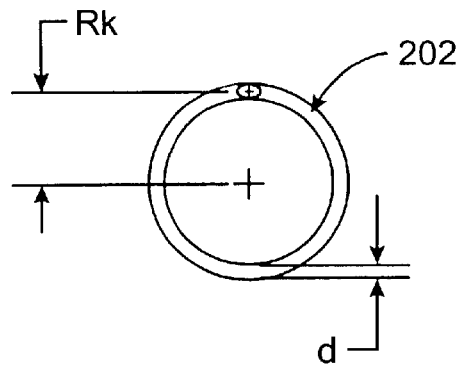
FIG. 1c
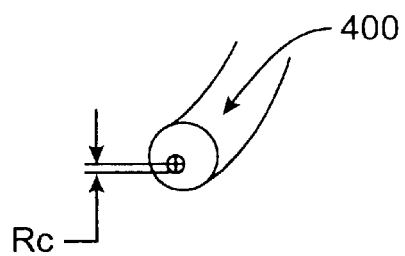
FIG. 1c'
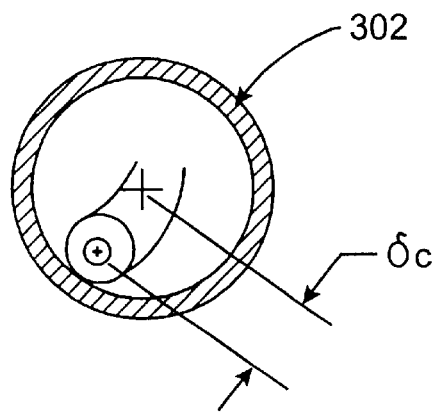
FIG. 1c"

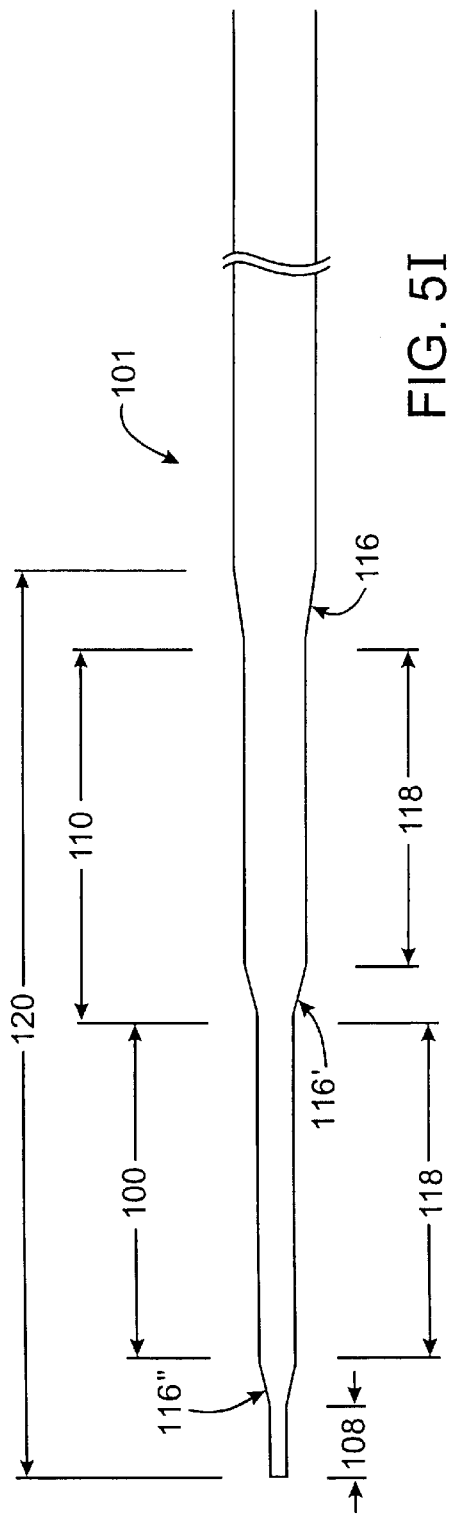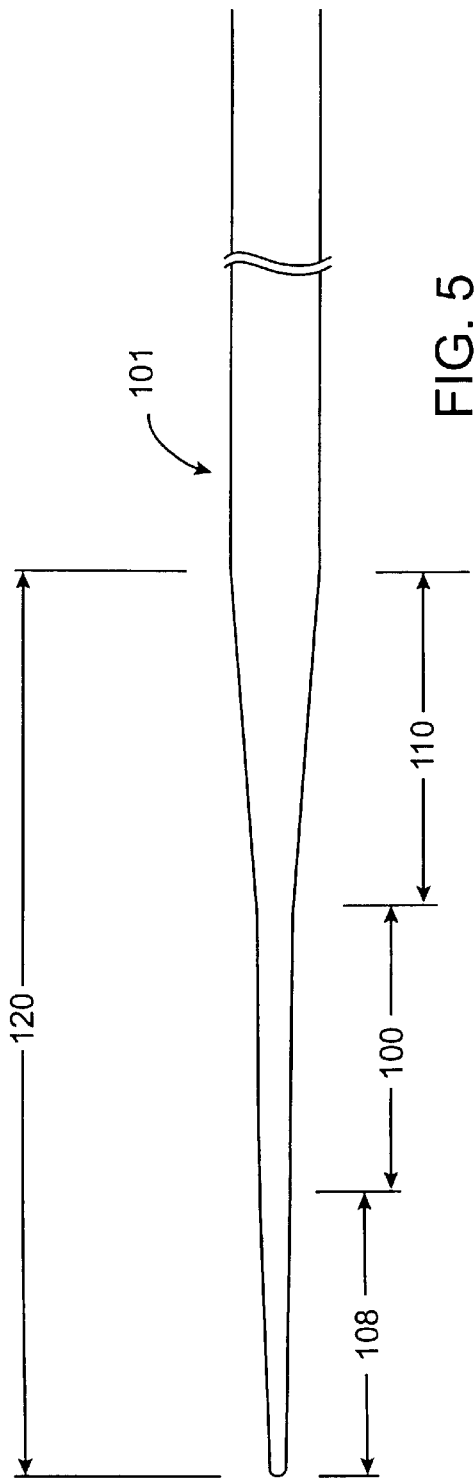
FIG. 5I
FIG. 5

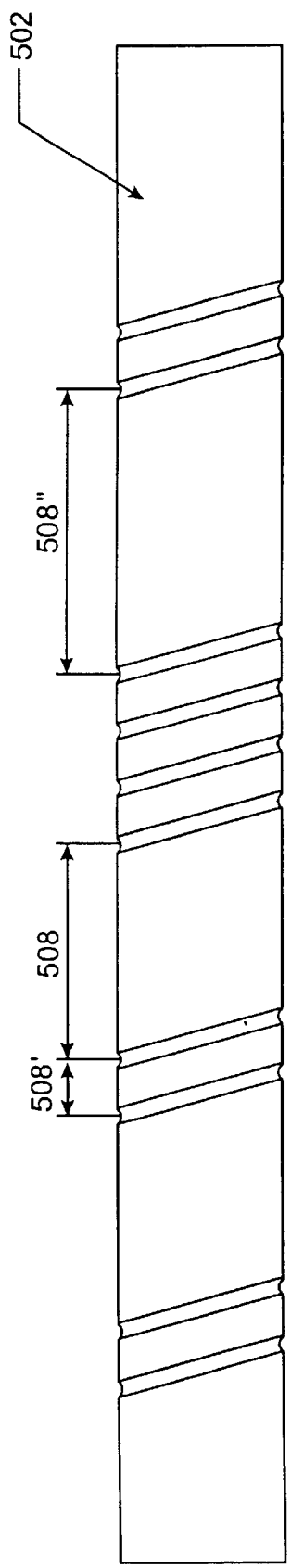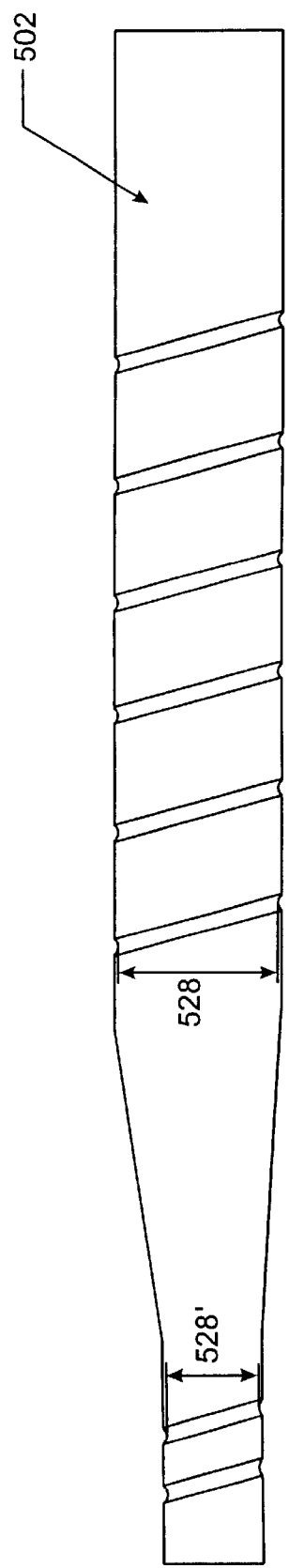

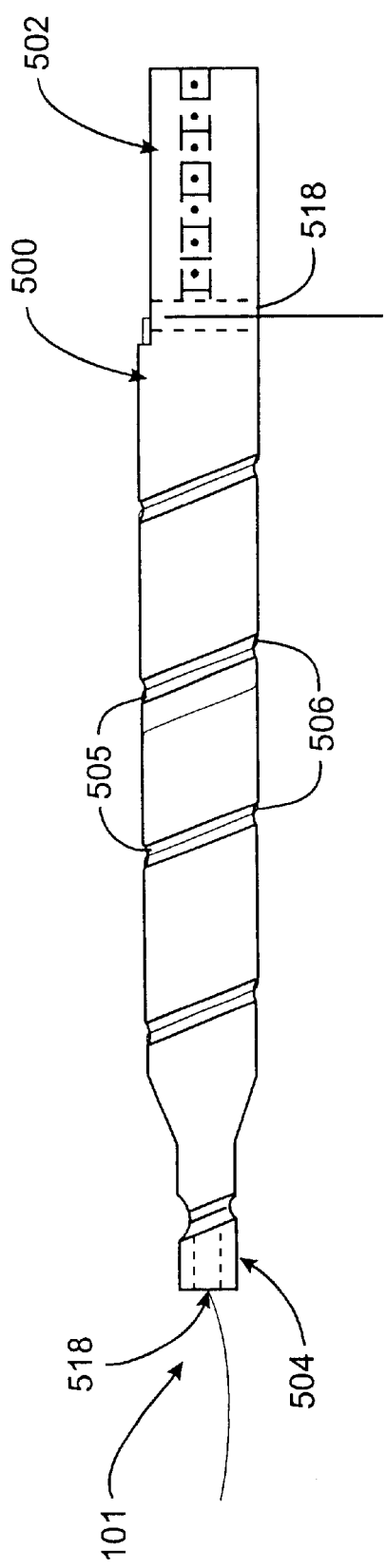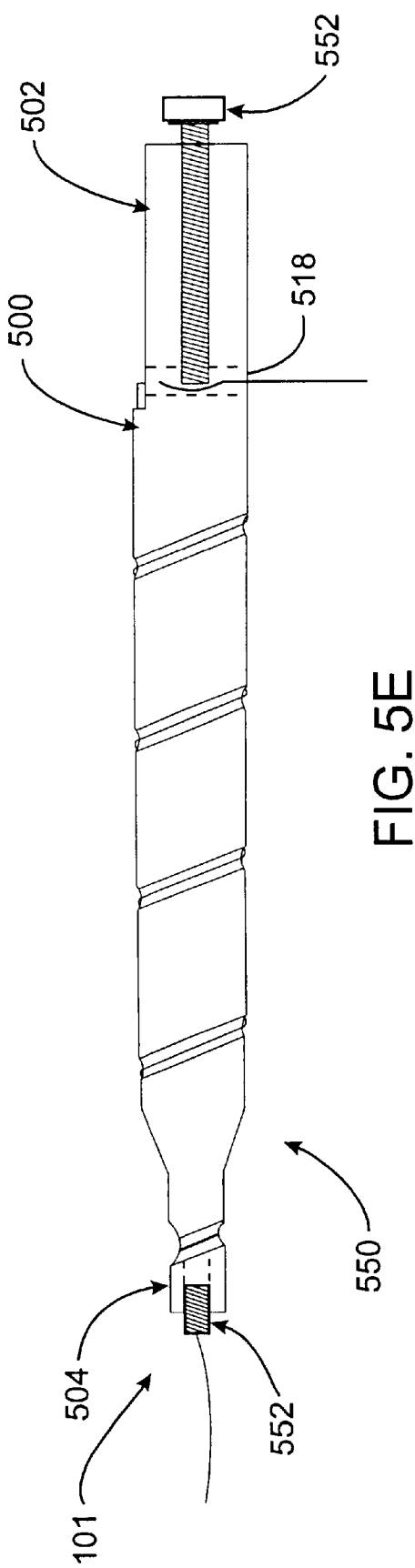
FIG. 5D
FIG. 5E

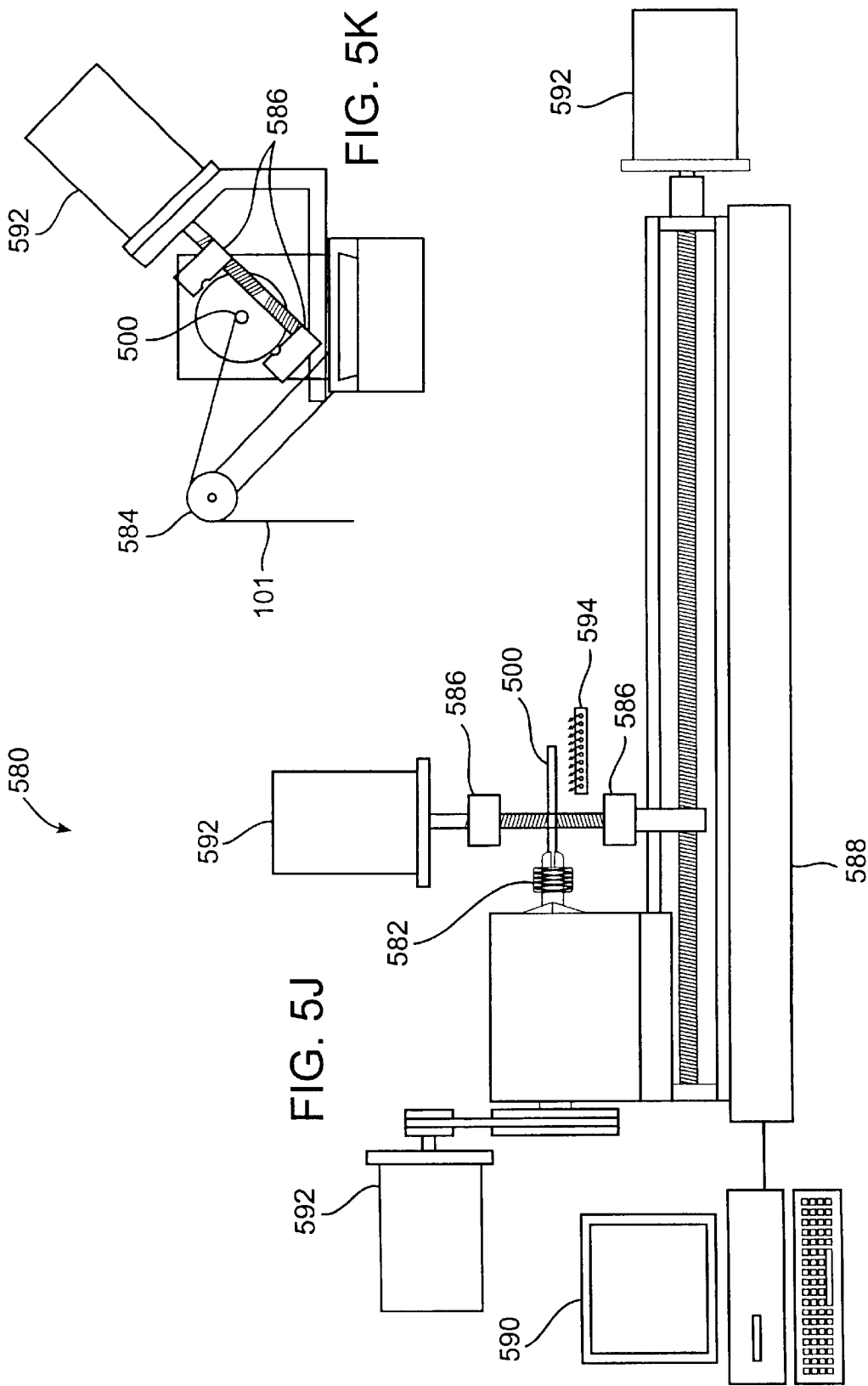

GUIDEWIRE FOR POSITIONING A CATHETER AGAINST A LUMEN WALL

CROSS-REFERENCES TO RELATED APPLICATIONS

This application is a continuation-in-part of U.S. application Ser. No. 09/289,850, filed Apr. 12, 1999, which claimed the benefit of U.S. provisional application No. 60/081,631 filed Apr. 13, 1998; U.S. provisional application No. 60/081,614 filed Apr. 13, 1998; and U.S. provisional application No. 60/103,447 filed Oct. 7, 1998; which is a continuation-in-part of U.S. application Ser. No. 08/966,001 filed Nov. 7, 1997, now U.S. Pat. No. 6,156,046; which is a continuation-in-part of U.S. application Ser. No. 09/290,510 filed Apr. 12, 1999 now U.S. Pat. No. 6,139,557, which claimed the benefit of U.S. provisional application No. 60/081,631 filed Apr. 13, 1998; U.S. provisional application no. 60/081,614 filed Apr. 13, 1998; and U.S. provisional application No. 60/103,447 filed Oct. 7, 1998; now U.S. Pat. No. 6,139,557; and which is a continuation-in-part of U.S. application Ser. No. 09/389,772 filed Sep. 3, 1999, of which claimed the benefit of U.S. provisional application No. 60/099,079 filed Sep. 4, 1998. The full disclosures of each of these prior regular and provisional applications are incorporated herein by reference.

BACKGROUND OF THE INVENTION

1. Field of the Invention

The present invention relates generally to an apparatus and method of making a guidewire with a preformed three dimensional profile for use in guiding a catheter or other medical device to a desired location within a body lumen.

2. Description of the Background Art

Medical guidewires are used primarily to facilitate the placement of catheters and endoscopic instruments within the tortuous paths of body conduits. For example, if it is desirable to place a catheter within the vascular system of a patient, a guidewire is first inserted into the vessel and then guided through the tortuous path desired for the catheter. Then the catheter is threaded over the guidewire. As the catheter is advanced it tends to follow the direction of the guidewire so that it ultimately negotiates the same tortuous path. Once the catheter is in its final operative position, the guidewire can be removed leaving the catheter to perform its desired function.

Guidewires are traditionally utilized to negotiate the complex vascular system of a patient to guide a medical device, (e.g., a catheter) to a desired location. It has been in the past of paramount importance for the guidewire to have a shape which provides for superior navigation a patient's vascular system. Inventions in the field include guidewires with floppy tips, improved methods of manufacturing, increased torqueability and improved friction reducing features to help catheters move over the guidewires. Thus the focus of the prior art has been to create a guidewire with the ability to create a path along which a catheter could follow to reach a particular site of the body.

Guidewires often use transition areas of changing diameter along their length. A smooth transition gives the guidewire the ability to better negotiate tight bends in the anatomy of the patient. The transition area of a guidewire may be long or short, that is the change from one diameter along the length of the guidewire may occur over a few millimeters, or several centimeters. In the past the use of transition areas has been combined with the use of a filament wire which covers the narrower distal section of the guidewire. The combination, well understood in the art, provides the distal tip of the wire with a greater flexibility to steer through the vasculature of a patient, while the filament wire provides added strength and radiopacity. The filament wire can also be used as a fastening point for the attachment of an atraumatic tip. Examples of guidewires using the combination of transition areas and filament wires are described in Colon et al., (U.S. Pat. No. 5,402,799) and Ashby et al., (U.S. Pat. No. 5,622,184). Others have modified the basic design by using other materials, such as Johanson et al., (U.S. Pat. No. 5,596,996). However all of the prior art to date has used guidewires for essentially the same purpose, to navigate the anatomy of a patient and direct a catheter to a particular sight within a body lumen. The medical procedure to be carried out is then conducted by the catheter. There are specialized guidewires which have been developed which attempt to do the job of a catheter using a modified guidewire. Two examples are guidewires with imaging and non-imaging sensors.

However there remains a need for a guidewire which can steer a catheter more particularly to a precise position within the vascular system of the patient. More particularly it would be beneficial to be able to manufacture a guidewire able to direct a catheter to a particular side of a lumen in the event a physician wishes to treat one side of a body lumen and not another, or be able to direct a catheter to precise locations of a body lumen. Straight guidewires are unable to perform this feat, however a novel guidewire has been disclosed in co-pending patent application Ser. No. 08/966,001 which is capable of steering catheters to a particular side of a body lumen. At least some of these objectives will be met by the embodiments of the present invention described below.

SUMMARY OF THE INVENTION

The present invention relates to medical wires, specifically guidewires and perfusion wires. In general the wires share a generally straight proximal section and a distal section having a curved three dimensional profile. The three dimensional profile usually defines a helical section having a relaxed diameter and a constrained diameter. The use of various materials and manufacturing techniques produces the variety of wires disclosed.

In a first embodiment, a guidewire for guiding another device to a desired location within a body lumen is described. The guidewire has a generally straight proximal section, and a guide section which defines a helical or other curved three dimensional profile. The three dimensional profile of the guide section is diametrically larger than the profile of the proximal section. The guide section is preferably made from a shape memory alloy and provides a curved path for another medical device to follow. The guide section has sufficient flexibility to assume a generally straight configuration when the guide section is extended through the lumen of a guiding member, such as a catheter, or is otherwise constrained.

In a second embodiment, a guidewire having a generally straight proximal section and a distal section having a helical support section is described. The helical support section defines a curved three dimensional profile that is diametrically larger than the proximal section. The helical support section is capable of elongation into a substantially straight profile when constrained and expansion into a wider diameter when unconstrained. The helical support section exerts an outward radial force ($W_r$) less than 20 pounds per inch, preferably less than 15 pounds per inch, usually less than 10 pounds per inch, and often less than 5 pounds per inch when axially extended so the diameter of the helical guide section is half the relaxed diameter. Exemplary ranges of outward radial force are from 0.001 pound per inch to 3 pounds per inch, usually from 0.01 pound per inch to 1 pound per inch.

In a third embodiment, a perfusion wire is disclosed with a generally straight proximal section and a distal section having a helical support section. The helical support section defines a curved three dimensional profile that is diametrically larger than the diameter of the proximal section. The helical perfusion section is capable of elongation into a substantially straight profile hen constrained and expansion to a larger diameter ($W_r$) when unconstrained. The helical perfusion section exerts an outward radial force in excess of 10 pounds per inch, preferably 20 pounds per inch, and often 100 pounds per inch, or higher, when axially extended so the constrained diameter is half the unconstrained diameter.

A system is described comprising a guidewire having a straight proximal section and a distal section. The distal section having a helical guide section capable of changing geometry when constrained in a lumen. The helical guide section exerts and outward radial force less than 15 pounds per inch, preferably less than 15 pounds per inch, usually less than 10 pounds per inch, and often less than 5 pounds per inch. Exemplary ranges of outward radial force are from 0.001 pound per inch to 3 pounds per inch, usually from 0.01 pound per inch to 1 pound per inch. A catheter is included in the system that is capable of tracking over the guidewire wherein the catheter is capable of following the three dimensional profile of the helical guide section. The catheter exerts an outward radial force ($P_{eff}$) on a lumen at substantially the point of entry of the guidewire into the catheter, thus causing the catheter to exert an outward radial force less than 4 pounds per inch, preferably less than 2 pounds per inch, usually less than 1 pound per inch. Exemplary ranges of outward radial catheter force are from 0.0001 pound per inch to 2 pounds per inch, usually from 0.001 pound per inch to 1 pound per inch. The precise outward radial force can be determined using an equation.

The guidewire of the present invention may be manufactured using an apparatus comprising a mandrel with a heat stable core. The mandrel has at least one screw thread having spaced apart roots for receiving a guidewire. The mandrel also has at least one retainer for ensuring the guide wire is securely fixed to the mandrel. The method of using the apparatus follows the steps of wrapping a guidewire around the mandrel, securing the wire about the mandrel with the retaining device, heating the mandrel to a desired temperature, stopping the heating, cooling the mandrel and unwrapping the wire from the mandrel. A system for automating the manufacturing process is also described.

These and other embodiments are further detailed in the descriptions that follow.

BRIEF DESCRIPTION OF THE DRAWINGS

FIG. 1A shows a plan view of a unconstrained guide section.

FIG. 1B shows a constrained guide section.

FIG. 1C shows three key relationships in a simple visual format.

FIGS. 5 and 5I show two core wire geometries prior to treatment according to the present invention.

FIGS. 5A–5H illustrate various mandrels and mandrel assemblies.

FIGS. 5J and 5K show a system for automated manufacturing of the guide section.

DESCRIPTION OF THE SPECIFIC EMBODIMENTS

Figure 1D:
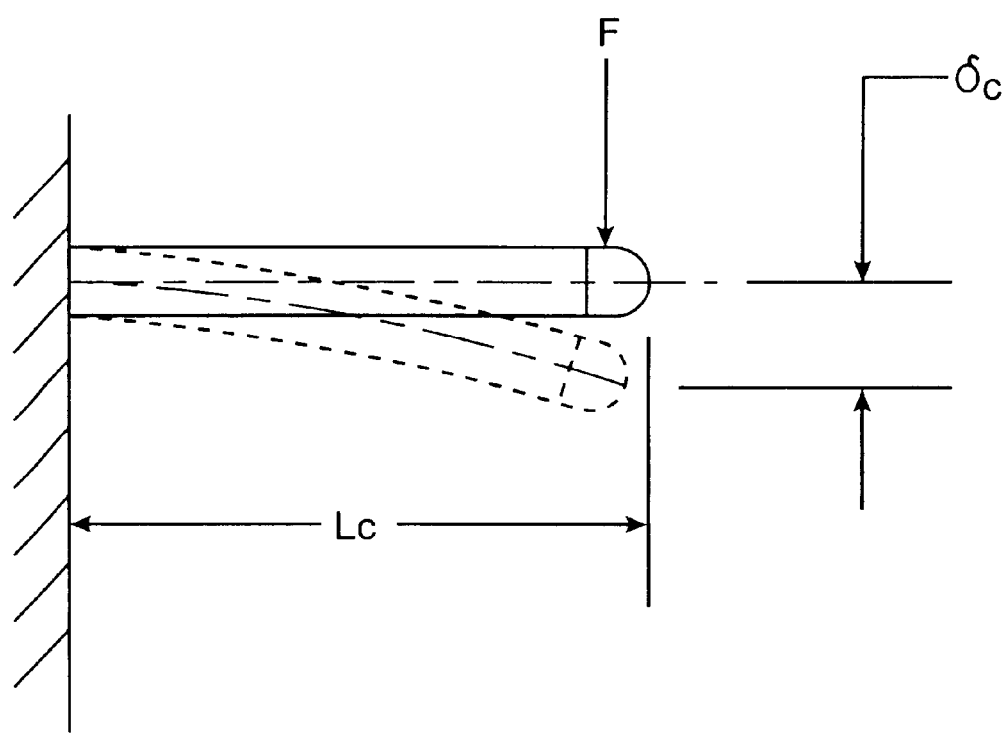
FIG. 1D show the beam stiffness variables for a catheter.

The following detailed descriptions are the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

1. Definitions and Table of Variables

While common guidewire terminology is used herein, clarification of certain terms are necessary. Terms used in the field of guidewire manufacturing and guidewire usage often vary among physicians and practitioners. The present invention is designed to take a straight core wire and reshape it into a form suitable for use in interventional procedures. The "core wire" is the back bone of a guidewire. Frequently made from a bio-compatible alloys such as stainless steel or nickel-titanium, these wires are usually larger at the proximal side and tapered to a thinner diameter at the distal end. The taper of the guidewire can be constant along the length, or broken up into transition lengths. Along the distal tip of the guidewire, a small coil is often slid over and secured to the core wire. The small wire which is used to make the coil is referred to herein as the "filament wire." The diameter of a regular guidewire used in cardiology procedures at the present time is generally about 0.014." For purposes of discussion the core wires used in the present invention follow the same geometries of the core wires used in other guidewires.

A tapered core wire is used as the starting material for making a guidewire having a three dimensional profile. By "three dimensional profile" we refer to the shape the wire assumes after it has gone through the procedure detailed below. Once the shape setting step is complete, the core wire can be modified as any other guidewire may be by techniques well understood in the art. While most guidewires are used to guide a catheter from a point of entry from outside a patients body to a desired location, the guidewire of the present invention is preferably utilized to direct a catheter to precise locations in a body lumen after the catheter has already been guided to the general site of interest using a standard guidewire. The present invention may be used for both introducing the catheter and for localized guidance if the guidewire is composed of a two way shape memory material.

Shape memory alloys are commonly used in medical devices. Shape memory alloys are often used for making guidewires and stents. A wide variety of shape memory alloys are currently available (see Table 1). Among the more common alloys used is nickel-titanium. The principle feature these alloys possess is their ability to deform in a super elastic range. This alloys these alloys to change their shape to a greater degree than other materials, without being permanently deformed. This ability makes shape memory alloys a preferred material for the present invention. However the present invention does not depend on super elastic properties and can function with in the elastic range of standard metal alloys such as stainless steel. Furthermore full recovery of the material is not necessary so materials may also operate according to the present invention with a small degree of plastic deformation.

TABLE 1

Shape Memory Alloys

| Alloy | Sample Composition | Transformation–Temp Range (Degrees Celsius) |
| --- | --- | --- |
| Ag—Cd | 44/49 at. % Cd | −190 to −50 |
| Au—Cd | 46.5/50 at % Cd | 30 to 100 |
| Cu—Al—Ni | 14/14.5 wt % Al 3 to 4.5 wt % Ni | |
| Cu—Sn | 15 at. % Sn | −120 to 30 |
| Cu—Zn | 38.5/41.5 wt % Zn | −180 to −10 |
| Cu—Zn-X | (X = a few wt % Si, Sn, Al) | −180 to 200 |
| In—Ti | 18/23 at % Ti | 60 to 100 |
| Ni—Al | 36/38 at. % Al | −180 to 100 |
| Ni—Ti | 49/51 at % Ni | −50 to 110 |
| Fe—Pt | 25 at % Pt | −130 |
| Mn—Cu | 5/35 at % Cu | −250 to 180 |
| Fe—Mn—Si | 32 wt % Mn, 6 wt % Si | −200 to 150 |

Examples of superelastic metal alloys, including nickel-titanium, which are usable to form the core of the guidewire of the present invention are described in detail in U.S. Pat. No. 4,665,906. The disclosure of U.S. Pat. No. 4,665,906 is expressly incorporated herein by reference insofar as it describes the compositions, properties, chemistries, and behavior of specific metal alloys which are super elastic within the temperature range at which the guide section of the guidewire of the present invention operates, any and all of which super elastic metal alloys may be usable to form the core of the guide section of the guidewire.

Regardless of the materials used the helical guide section or perfusion section according to the present invention will exert an outward radial force ($W_r$) when constrained to a helical radius less than the unconstrained helical radius. The variables that are used to determine the outward radial force ($W_r$) of the helical guide section and the perfusion section, as well as the force a catheter exerts at the point of contact ($P_{eff}$) over a helical guide section are given in Table 2.

TABLE 2

Variables for Determination of $W_r$ and $P_{eff}$

| Symbol | Definition |
| --- | --- |
| $P_{eff}$ | Force the distal end of the catheter exerts against the lumen wall |
| D | Diameter of the wire comprising the guide section |
| R | Radius of guide section measured from axis of guide section |
| $R_0$ | Initial radius of guide section measured from axis of guide section |
| $R_k$ | Distance between the axis of the helical guide section and the center of the wire comprising the helical guide section |
| $S_{tot}$ | Total length of wire used to make the helical guide section |

TABLE 2-continued

Variables for Determination of $W_r$ and $P_{eff}$

| Symbol | Definition |
| --- | --- |
| N | Number of active turns in guide section |
| $E_g$ | Modulus of elasticity of the wire comprising the guide section |
| $I_g$ | Moment of inertia of the wire comprising the guide section |
| G | Shear modulus of elasticity of the wire comprising the guide section |
| $F_a$ | Axial force |
| $\delta_a$ | Axial displacement of the guide section |
| $R_c$ | Radius of the center lumen of the catheter through which the guide wire passes |
| $L_c$ | Effective length of the catheter in bending |
| $E_c$ | Modulus of elasticity of the catheter |
| $I_c$ | Moment of inertia of the catheter |
| $\delta_c$ | End displacement of catheter |
| $L_{eff}$ | Effective length of contact between the distal section of the catheter and the lumen wall |
| $W_r$ | Outward radial force of a helical support section when constrained |

By "outward radial force" the description means a force exerted by a compressed helical guide section as it seeks to recover the strain it has experienced while being compressed. There are two predominate sources for compression of the helical guide section. First the helical guide section may be deployed within a lumen having a smaller diameter than the unconstrained diameter of the helical guide section. Under this condition the entire helical guide section may experience a uniform compression or constraining force preventing the helical guide section from releasing the strain energy it possesses. The outward radial force can be uniform along the entire length of the helical guide section, or can vary based on the amount of compression the guide section is experiencing. The second manner a guide section experiences compression, causing an outward radial force, is when a catheter tracking over the guide section causes further compression of the guide section. As the catheter advances, local deformations immediately proximal and distal to the catheter appear on the length of the guide section. These deformations are the result of the strain the catheter exerts on the guidewire as it is advanced. The guide section seeks to resist deformation and recover the strain to return to its natural, relaxed shape. Any force the guide section exerts as it seeks to recover its natural state is an "outward radial force" with respect to the intended operation and usage of the present invention. The outward radial force of the guide section less the beam stiffness of the catheter and the adjustments for the local deformations of the guidewire as the catheter is tracking over it constitute the value ($P_{eff}$).

A "catheter resistance force" is the force the catheter exerts on the guide section. This resistive force is a result of the catheter being displaced by the guide section off of its natural axis. The catheter may be stiff or flexible in the distal end as it moves over the guidewire. The stiffer the catheter, the greater the force the catheter exerts on the guide section. Any force the catheter exerts on the guide section at the distal tip of the catheter moving forward is the "catheter resistance force" with respect to the intended operation and usage of the present invention.

Referring now to FIG. 1A, the helical guide section 202 is shown in an unconstrained state. When the helical guide section 202 is unconstrained, it is possible to measure the radius $R_o$ of the helical guide section 202. $R_o$ is measured from the center axis of the guide section 212 to the outside of the wire comprising the helical guide. The total length of the wire comprising the helical guide section ($S_{tot}$) can either be measured directly from the straightened helical guide section or calculated using geometric relationships and measured parameters of the helical guide section 202. The total number of active coils of the helical guide section (N) can be measured directly from the helical guide section 202. The diameter of the wire 202d comprising the helical guide section 202 can be measured directly from the wire comprising the helical guide section. Lastly, the shear modulus of elasticity of the wire (G) may be determined from any readily available engineering reference manual.

FIG. 1B shows the helical guide section 202 axially extended so the constrained radius R is half the unconstrained radius $R_o$. At this time it is possible to measure or calculate the distance from the center axis of the helical guide section 212 to the center of the wire comprising the helical guide section ($R_k$) (FIG. 1C). The axial displacement of the helical guide section ($\delta_a$) 216c is the axial extension of the helical guide section 202 as a result of the helical guide section 202 being constrained by a lumen 300 of a certain radius (R). Because the helical guide section 202 is in contact with the wall of the lumen 302, the helical guide section 202 conforms to the radius of R. Conversely, when an axial force $F_a$ is applied to the helical guide section 202, the result is an axial displacement $\delta_a$ that will also result in the helical guide section 202 reducing to the radius of R. The two situations are equivalent in terms of the mechanical response of the helical guide section 202. The axial force ($F_a$) applied to the helical guide section 202 results in the axial displacement $\delta_a$.

The beam stiffness of the guidewire is needed to determine the outward radial force ($W_r$). In the system of the present invention a determination of the catheter stiffness is also required. Using a standard beam stiffness test it is possible to calculate or measure the beam stiffness of a catheter. The effective beam length of the catheter in bending ($L_c$) can also be measured. Finally it is necessary to determine the effective length of contact between the catheter distal end 406 and the wall of the lumen ($L_{eff}$). Once the beam stiffness measurements or calculations are completed, it is possible to determine the modulus of elasticity and the moment of inertia for both the helical guide section 202 and the catheter 400. These calculations produce the necessary EI data to determine $W_r$ and $P_{eff}$. The details of determining $W_r$ and $P_{eff}$ are described below in section 7 and 8 respectively.

FIG. 1C shows the value of $R_k$ as the distance from the axis of the helical guide section 212 to the center of the wire comprising the helical guide section 202. FIG. 1C' shows $R_c$ as the radius of the center lumen of the catheter 400 through which the guidewire 200 passes. FIG. 1C" shows $\delta_c$ as the displacement of the catheter 400 from its neutral, undeflected axis. The catheter is shown in the drawing in a perspective view with the front along the lumen circumference. For clarity the helical guide section 202 is not shown in this figure.

FIG. 1D shows the catheter under going a beam stiffness test (also known as a cantilever test) where $L_c$ is the effective beam length, F is the force applied to deflect the tip of the catheter 402 a distance $\delta_c$.

2. Guidewire with Curved Three Dimensional Profile

Figure 2A:
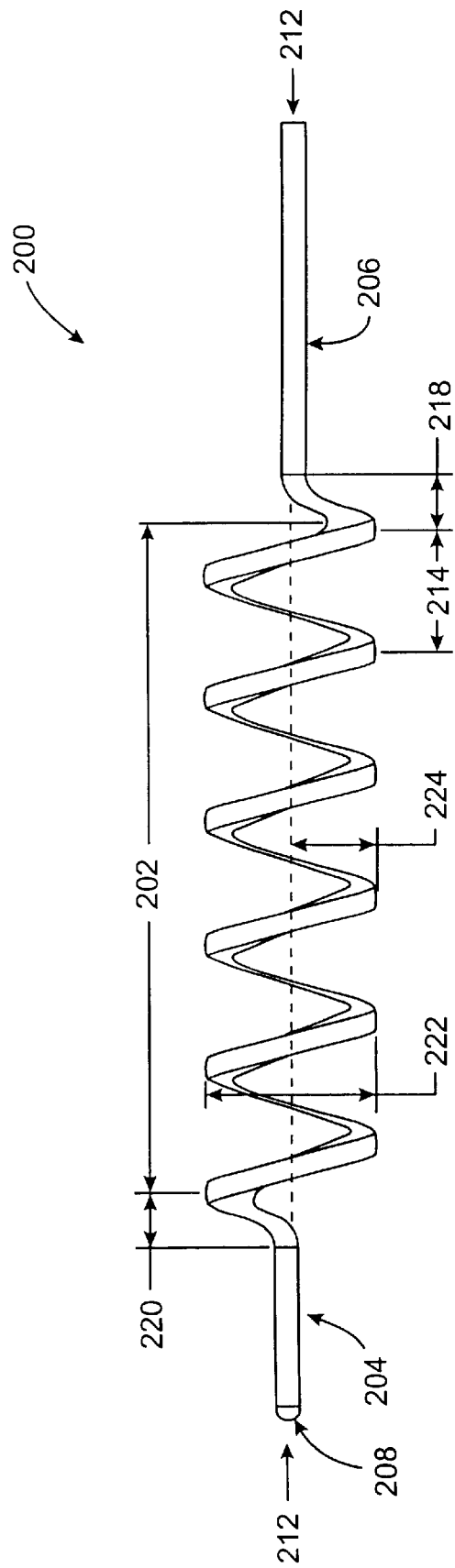
FIGS. 2A and 2B show a guidewire with a helical guide section.

FIG. 2A illustrates an embodiment of a guidewire 200 according to the present invention. The guidewire 200 is preferably provided with a configuration to enable it to guide, in a controlled manner, a catheter distal tip 402 (not shown) at and along the location of a body lumen 300.

Figure 2B:
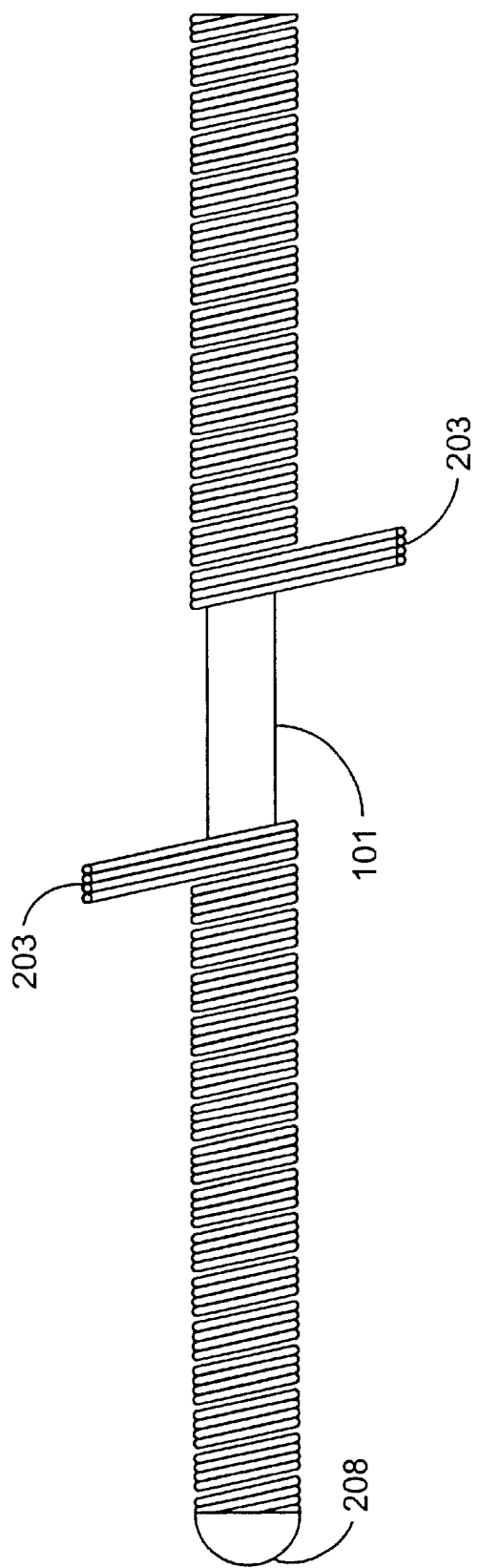

Referring to FIGS. 2A and 2B; the guidewire 200 is provided with a generally helical guide section 202 adjacent its distal end 204. As shown in FIG. 2A, the helical guide section 202 has a three-dimensional configuration that approximates the configuration of a cylindrical lumen wall. The distal end 204 of the guidewire 200 is generally straight and preferably has an atraumatic distal tip 208. The remainder of the guidewire 200, and in particular, the proximal section 206, is generally straight, as with conventional guidewires. The distal section 204 and the proximal section 206 are axially coplanar with each other, and are preferably coaxial with respect to each other. In other words, the distal section 204 and the proximal section 206 are oriented along the same longitudinal axis. In addition, the distal section 204 and the proximal section 206 are concentric, and can also be eccentric, with respect to the guide section 202. The proximal and distal extremities of the helical guide section 202, or the entire helical section, are preferably provided with sufficient radiopacity so that the helical guide section 202 can be clearly viewed during fluoroscopic visualization. The radiopacity can be provided by the use of a radiopaque wire 203, as shown in FIG. 2B, which can be made of platinum or gold alloys or other radiopaque wires, and which is wound around the core wire 101.

The helical guide section 202 of the guidewire 200 can be modified so that it has a generally tapered or stepped, or both tapered and stepped, configuration (not shown). For example, the helix of the guide section 202 can be tapered from the proximal extremity to the distal extremity thereof so that the helical diameter decreases from the proximal extremity to the distal extremity. The helix can also be stepped at certain discrete locations of the guide section 202. In addition, although the helical guide section 202 of the guidewire 200 is illustrated as having uniformly configured helixes, it is also possible to provide the helixes in a manner that they are non-uniform to each other across the helical length 202.

As yet another alternative, a plurality of guide sections 202 can be provided in spaced-apart manner at the distal end of the guidewire 200. For example, two spaced-apart guide sections 202 would be helpful in treating body lumens where restenosis has occurred at the locations of two spaced-apart implanted stents.

3. Guidewire Having a Helical Guide Section with a Low Radial Force

Figures 3A, 3B, 3C:
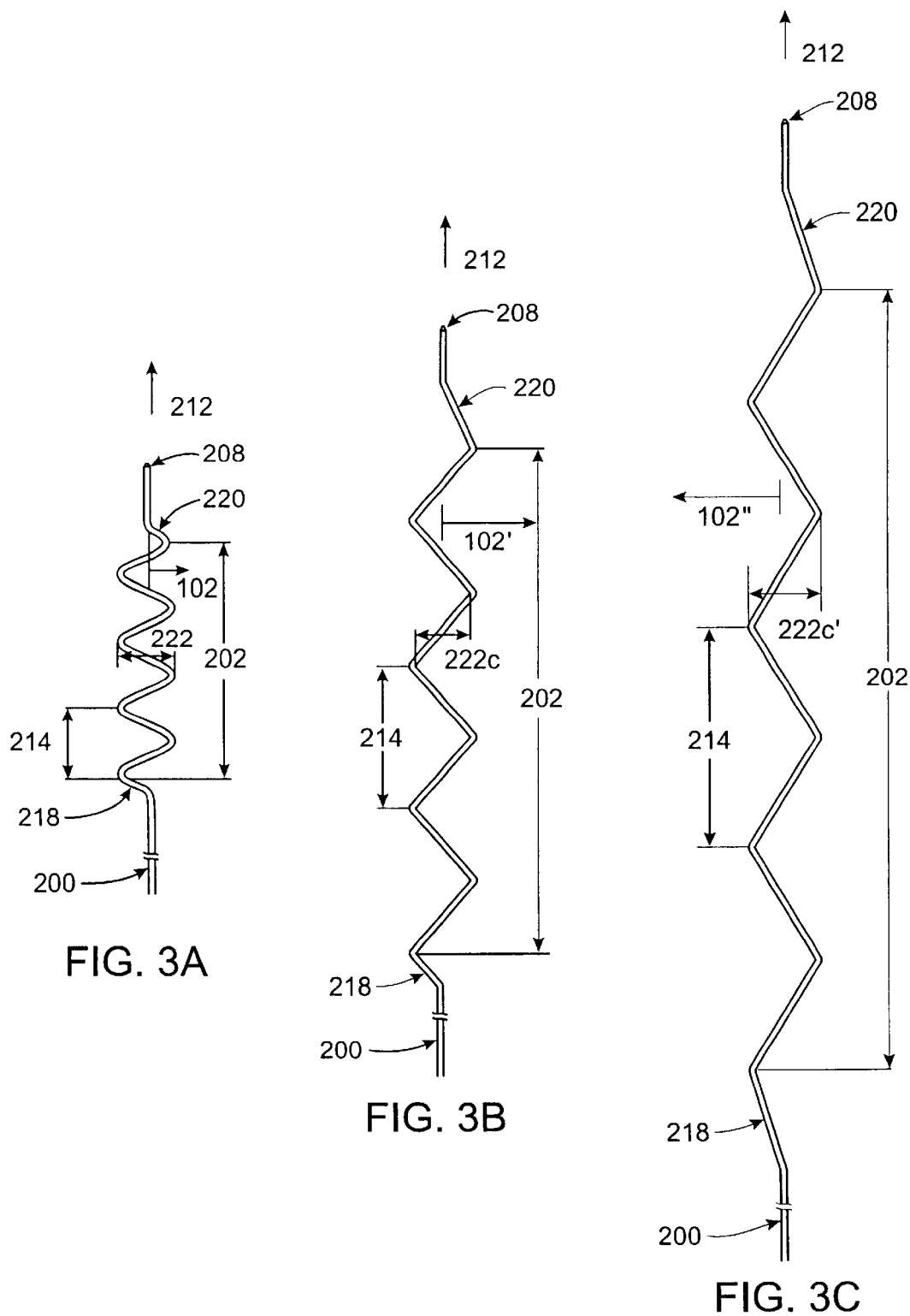
FIGS. 3A, 3B, and 3C shows a guide section with reference to the elements for a low outward radial force ($W_r$).

FIGS. 3A, 3B, and 3C show the preferred embodiment of the present invention. A guidewire 200 with an atraumatic tip 208 is shown with a helical guide section 202 capable of exerting an outward radial force ($W_r$) 102 when compressed. The vectors 102, 102' and 102" represent the larger radial forces generated from the increased compression of the helical guide section 202. It is important to note that while the drawings show these as vector arrows, the outward radial force ($W_r$) is a distributed force along the entire length of the helical guide section 202. The helical guide section 202 further comprises a plurality of helical winds 214 with a proximal transition period 218 and a distal transition period 220. The helical guide section 202 also has a relaxed helical diameter 222 and an axis of extension 212. The guidewire 200 has a core wire 101 made of a shape memory material such as nickel-titanium or other shape memory alloy. The actual outward radial force ($W_r$) of the helical guide section 202 depends on the composition of the helical guide section 202 when it is made, the shape it is fashioned into, and the amount of constraint it experiences. In general for interventional procedures the total outward radial force ($W_r$) must be sufficient to provide a force that can deflect a catheter tip 402 (not shown) in a controlled manner to abut a lumen wall 302 while at the same time not damaging the lumen wall 302.

9

The helical guide section 202 exerts an outward radial force ($W_r$) when compressed which is proportional to the axial extension of the helical guide section 202. The outward radial force ($W_r$) is distributed along each helical wind 214 of the guide section 202 in proportion to the radial compression of the particular wind. That is, those helical winds 214 that are more compressed, will have a greater outward force ($W_r$). Since it is difficult to accurately measure the force values of the helical guide section 202 in vivo (when it is compressed inside a body lumen), the current description uses a test model in an in vitro setting. That is a bench top test is used to determine the force values of the helical guide section 202. In general the helical guide section 202 has a maximum outward radial force ($W_r$) less than fifteen (15) pounds per inch when constrained to a radius that is half the unconstrained radius. Preferably the outward radial force ($W_r$) is in between of 0.0001 pound and 3.0 pounds. The actual outward radial force ($W_r$) of the helical guide section 202 can be calculated using the formula:

$$W_r = (((E_g I_g) F_a \delta_a)/(2 S_{tot} R_k R_o R^2))^{1/2}$$

Wherein the formula variables are defined above.

4. System with Guidewire and Catheter

Figure 4:
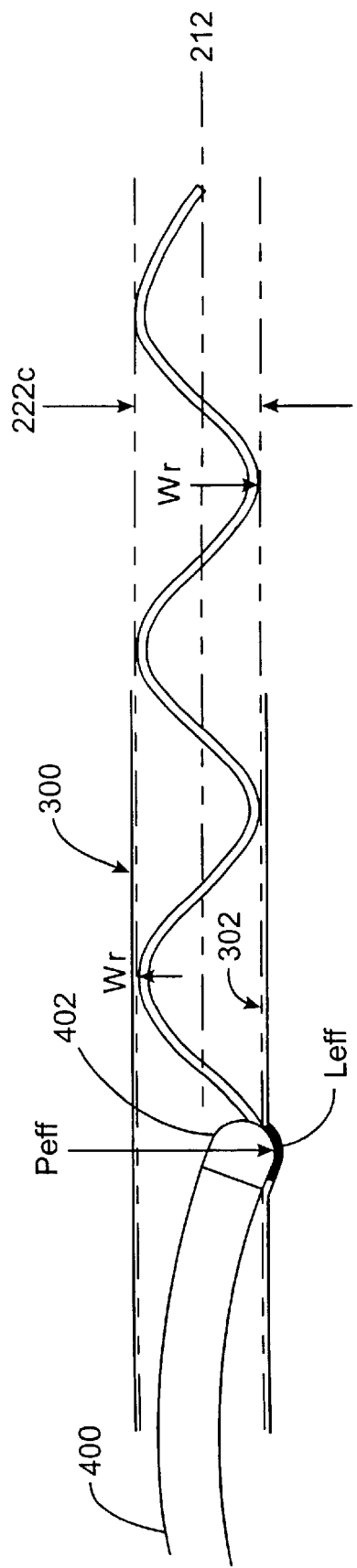
FIG. 4 shows the relationship between a catheter, guidewire and lumen.

FIG. 4 illustrates the relationship between the guide section 202 and the catheter distal tip 402. Competing factors must be considered when the helical guide section 202 is made. A helical guide section 202 having a helical diameter 322 smaller than the vessel it may operate in will not provide the necessary relationship between the guidewire 200 and a catheter distal tip 402 to provide precision location of the catheter distal tip 402 in a lumen 300. Likewise if the core wire 101 is too stiff, the helical guide section 202 will not deform when the catheter distal tip 402 tracks over it. In general the helical guide section 202 of the present invention will operate using materials generally the same as used for straight guidewires.

The use of a shape memory material in the helical guide section 202 allows the helical guide section 202 to be deformed in the elastic and super elastic range of the material and return to the original shape of the helical guide section 202. The inherent unloading of force, or relaxing of the helical guide section 202 when it is compressed, produces the outward radial force ($W_r$). The thicker the core wire 101 of the guidewire 200, the stronger the outward radial force ($W_r$), or the greater the resistance to deformation the helical guide section 202 possesses. The combination of elements and properties provide the guide section 202 of the guidewire 200 with an outward radial force ($W_r$) sufficient to deflect a catheter distal tip 402 into the lumen wall 302 as the catheter 400 is being advanced over the guide section 202. This relationship holds true as the helical diameter 322 of the guide section 202 compresses from its free state to conform to the lumen diameter.

When a catheter 400 is tracking over the guide section 202 while the guide section 202 is pushing against the lumen wall 302, the outward radial force the catheter exerts ($P_{eff}$) against the lumen wall 302 is determined from the value of the force the guide section exerts ($W_r$) plus a term for the energy release of the guide section and the torsional energy of the guide section less the catheter beam stiffness. The relationship can be expressed as:

$$P_{eff} = (((E_g I_g) F_a \delta_a)/(2 S_{tot} R_k R_o R^2))^{1/2}$$
$$(L_{eff}) + E_g I_g [((1/R_o) - (1/R_o) -$$
$$(1/R))((1/R_o R^2))]^{1/2} + ((96 F_a^2 R^2 N)/(d^4 G)) - ((3(E_c I_c) \delta_c)/(L_c^3)).$$

Wherein the variables are defined above.

10

5. Apparatus and Methods for Manufacturing Wire with a Helical Guide Section

FIGS. 5 and 5I illustrate a typical core wire 101 that has been ground down for use in the present invention. The core wire 101 has a tapered region 120 that begins at the most proximal grind down 116, or at the point the core wire begins to taper if the grind down is a gradual and constant type 110. In a step down grind configuration (FIG. 5I) of the core wire 101, the barrels 118 between step down grinds 116, 116' and 116" have a constant diameter. In the preferred embodiment, three step down regions are used. However the present invention may be made with a single grind down that is either gradual along the entire length of the grind down region, or of variable decreasing diameter along the length of the grind down region. It should be appreciated that the strength of the guide section of the wire will be decreased as the diameter of the core wire 101 is reduced. Thus it is preferred to maintain the core wire diameter along the length of the core wire to be consistent. The most distal barrel is the distal tip 108. The intermediate barrel 100 forms the guide section 202 after heat setting in the preferred embodiment. The proximal barrel is the proximal section 110. Proximal to the proximal grind 116 is unmodified core wire 101.

Figure 5A:
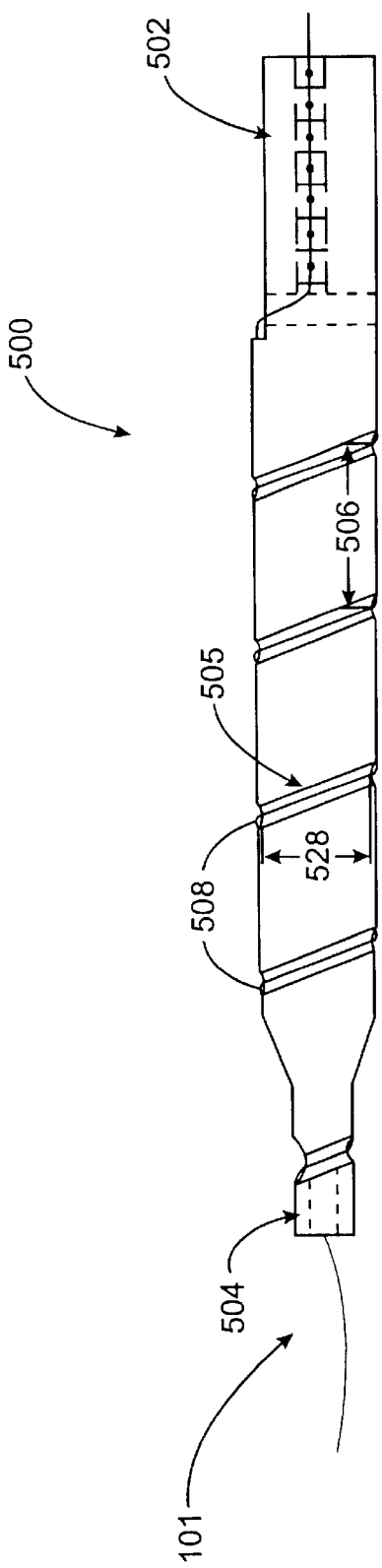

FIG. 5A illustrates a plan view of a mandrel 500 in its basic form. The mandrel 500 has a proximal end 502 and a distal end 504 for reference. A helical screw thread 505 is engraved into the mandrel 500. The screw thread 505 has a defined pitch 508 used to establish the distance between the coils of the core wire once the shape setting procedure is complete. The screw thread 505 has spaced apart roots 506 for receiving the core wire 101. It is important the mandrel 500 be made from a temperature stable material for the operation of making the shaped guidewire. The mandrel 500 may be made of brass, steel, ceramics or any other material which will retain its shape at temperatures up to 800 degrees Centigrade. The diameter of the mandrel between the bottom of the roots 506 is the minor diameter 528. The minor diameter 528 determines the minimum inner diameter of the core wire 101 after the shape setting is complete.

FIG. 5B shows a mandrel 500 with three different pitches 508, 508' 508" that can be used to produce a guidewire where the pitch is uneven along the length of the three dimensional profile of the wire. FIG. 5C shows another mandrel 500 where the diameter of the helical winds may be varied. Because of the ability of shape memory alloys to assume a tremendous assortment of shapes, the mandrel 500 may be designed with any combination of cross section geometries and diameters. However it should be apparent that the smoother the outer perimeter of the wire during usage, the less traumatic the guidewire will be to the patient. Thus it is preferred to utilize a regularly curved helical structure when possible.

FIGS. 5D and 5E show a series of drawings where the method of the present invention is employed to produce a guidewire having a shaped three dimensional profile. The mandrel 500 in FIG. 5D is shown with a core wire 101 being introduced into the proximal end 502. The winding procedure may be done by hand. If done by hand, the operator feeds a predetermined length of the core wire 101 through the wire entry port 518 on the proximal tip 502. Once the appropriate amount is fed through the first wire entry port 518, the core wire 101 is secured at the proximal end 502 with a securing means 552. The core wire 101 is wound around the screw threads 505 either by a machine or an operator, and the core wire 101 is wound tightly so tension remains in the core wire 101 during the shape setting procedure. The operator must be careful to make sure each wind in the roots 506 is tight. If the wire is not tightly wound around the mandrel 500 during the shape setting step the wire will not retain the shape of the mandrel 500. Alternatively the operator may feed any length of the core wire 101 through the first wire entry port 518 and simply clip off any excess core wire 101 that remains after the winding procedure.

FIG. 5E shows the core wire 101 fully wrapped around the mandrel 500. The core wire 101 is fed through both wire entry ports 518 on the distal tip 502 and the distal end 504. Once the core wire 101 is fully wrapped around the mandrel 500, a second core wire securing means 552 is used at the distal end 504 to make sure tension remains in the core wire 101 about the mandrel 500. The core wire 101 and mandrel 500 together comprise the mandrel assembly 550. The mandrel assembly 550 is then heated to the appropriate shape setting temperature which corresponds to that of the shape memory alloy being used. For nickel-titanium alloys, the temperature is preferably between 200 and 800 degrees Centigrade. In the case of two way shape memory alloys, the shape setting temperature should also be between 200 and 800 degrees centigrade while the transition temperature between austenite and martensite phases can be any temperature which is not the same as the heat set temperature.

Figure 5F:
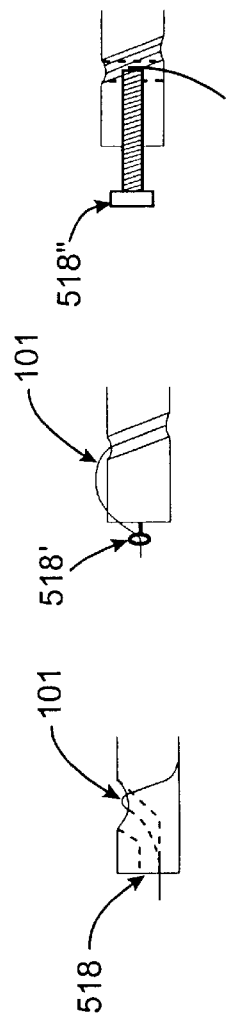

FIG. 5F shows the mandrel 500 with a variety of wire entry ports 518. The main consideration in the design of the wire entry port 518 is simply to be able to secure the core wire 101 to the mandrel 500 without damaging the core wire 101. Thus the wire entry port 518 may be a simple channel, an eyelet 518', threaded pin 518" or any other receptacle capable of holding the wire in place.

Alternatively, the core wire 101 may have a filament wire attached to it before the shape setting procedure is done. In the alternative method the core wire will have a filament wire tightly wrapped around the core wire, then be wrapped about the mandrel 500 as detailed above. Either method will produce the guidewire of the present invention. The completed shape set wire has a form similar to that shown in FIG. 2A.

Figure 5G:
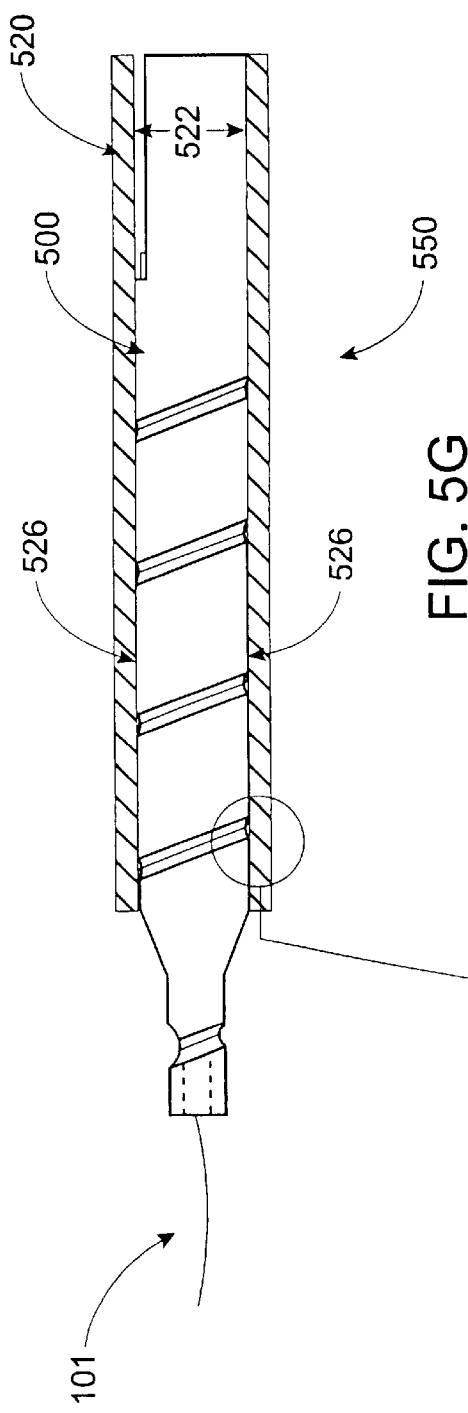
Figure 5H:
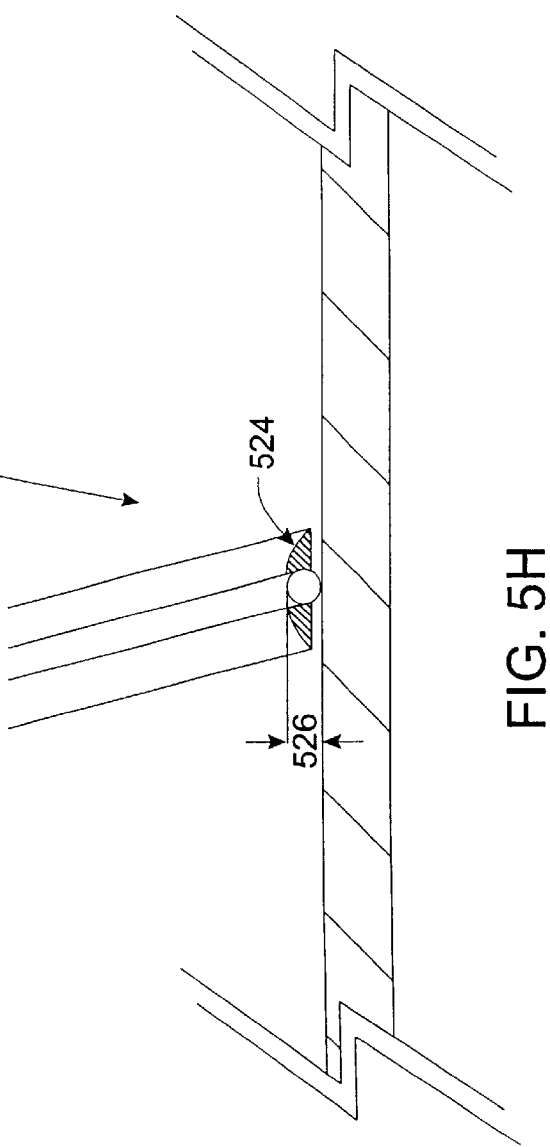
Figure 5L:
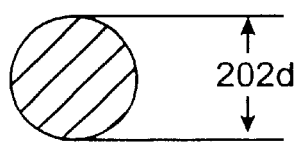
FIGS. 5L–5Q illustrate various cross sections of the guide section wire.

FIG. 5G shows another variation on the securing means used to provide the tension fit between the core wire 101 and the mandrel 500. A sleeve 520 with an inner diameter 522 frictionally engages the outer diameter of the mandrel 500 when the core wire 101 is wrapped around the mandrel 500. Using this embodiment it is necessary for the core wire 101 to be at least as high as the mandrel 500 outer surface so the core wire 101 can also frictionally engage the sleeve 520. Alternatively the sleeve 520 may have a heat stable cushion 524 (FIG. 5H) so that the cushion 524 may fill the gaps 526 in between the root 506 and the core wire 101. The sleeve 520 may be a cylinder or a foldable device which can be wrapped around the mandrel assembly 550 and then itself secured in place.

FIG. 5J shows a plan view of a system according to the present invention. The system 580 comprises a rotatable chuck 582 for holding the mandrel 500, and a spring tension arm 584 for maintaining the tension of the core wire 101 while the core wire 101 is loaded onto the mandrel 500. The system 580 also includes a heating element 586 for providing the heat necessary for accomplishing the shape setting step of the method described below. The rotatable chuck 582 may be turned by hand or mounted on a modified lathe 588. Furthermore the system 580 may be automated by using a computer controller 590 for handling the rotational speed of the chuck 582. Speed determination and the proper winding of the core wire 101 around the mandrel 500 is handled by a plurality of stepper motors 592. The heating element 586 need not be actual heaters, but can be any means known in the art to increase thermal temperatures, such as a salt bath, induction or RF system. An air cooling fan or blower 594 can be used to cool the mandrel 500 after the shape setting is finished. FIG. 5K shows an end view of the system described in FIG. 5J.

Figure 5M:
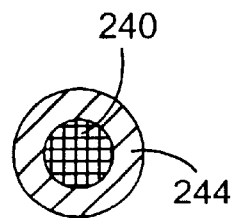
Figure 5N:
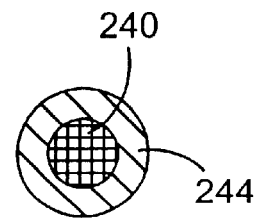
Figure 5O:
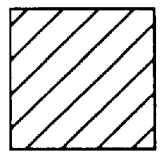
Figure 5P:
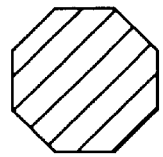
Figure 5Q:
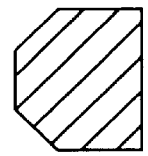

FIGS. 5L through 5Q show alternative core wires 101 which may be used in the present invention. Any material that can be shape set at a particular temperature, and has a high degree of elastic or super elastic behavior may be used in the current invention. Aside from a core wire of a single material or single alloy (FIG. 5L), the core wire may represent a complex structure such as a shape memory alloy hypo-tube 244 with a high density metal as the core 240 (FIG. 5M). An example would be a gold core wire with a nickel-titanium hypo-tube, the combination then being co-axial, and then the two being shape set using the method described above. The advantage of using a core wire comprising a sandwich or tube arrangement is greater radiopacity or lateral strength may be imparted to the core wire, depending on the particular desire of the manufacturer. FIG. 5N shows a shape memory alloy 240 as the core element and a different material 244 as the cladding. FIGS. 5O–5Q show three different cross sections for a shape memory alloy core wire 101.

When using the methods below for determining the outward radial force ($W_r$) and the force a catheter exerts on a lumen ($P_{eff}$) it should be noted that only the method for the most common wire diameter (FIG. 5L) has been detailed. The radial forces for a guide section with a non-circular cross section can be determined by simply adapting the methods below, and the formula to adjust for the change in the core wire cross-section.

6. Method of Determining the Outward Radial Force of a Helical Guide Section

A method of determining the outward radial force ($W_r$) of the guide section 202 using the physical and geometric properties of the helical guide section 202 as defined above and solving the following equation for $W_r$:

$$W_r = (((E_g I_g) F_a \delta_a)/(2 S_{tot} R_k R_o R^2))^{1/2}$$

As detailed above, the modulus of elasticity for the guide section ($E_g$) can be found in published sources. The moment of inertia for the guide section ($I_g$) can be calculated from the known geometry of the wire comprising the guide section 202. If the wire comprising the helical guide section 202 is a composite, the effective $E_g$ and $I_g$ can be calculated for the composite. The product of $E_g I_g$ in the first term of the equation for $W_r$ can alternately be determined empirically by performing a beam stiffness test on a section of the wire comprising the helical guide section 202.

The shear modulus of elasticity (G) for the guide section 202 can also be found in published sources. If the wire comprising the helical guide section 202 is a composite, the effective shear modulus of elasticity (G) can be calculated for the composite. Alternately, the shear modulus of elasticity (G) can be determined empirically by performing a torsional beam stiffness test on a section of the wire comprising the helical guide section 202.

Utilizing geometric relationships, the axial displacement of the guide section ($\delta_a$) and the distance between the axis of the helical guide section 202 and the center of the wire comprising the helical guide section ($R_k$) can be written in terms of the radius of the guide section measured from the axis 212 of the guide section to the outer edge of the guide section (R).

The axial force ($F_a$) can be expressed as $F_a = k \delta_a$, where k is the axial spring constant for the helical guide section 202.

As such, $F_a$ can be written in terms of R. Alternately, $\delta_a$ and $F_a$ can be determined empirically as a function of R: The axial force is measured by placing the guide section 202 in a force-displacement measuring instrument (such as an Instron™ model 5543, using a 10-pound load cell). The guide section 202 is subject to a standard axial force displacement test, with the ends of the guide section 202 fixed in rotation. The load cell of the Instron™ is slowly moved apart so that the guide section 202 of the guide section 202 is slowly stretched. The Instron™ can be programmed to measure on an incremental basis the force required to stretch the guide section 202. For example, if the guide section 202 is stretched at a rate of 1 cm per minute, force measurements can be taken every millimeter or every six seconds. Once the guide section 202 is extended to a point such that the guide section 202 is substantially straight, the test should be stopped.

Following completion of the axial force and displacement testing, the guide section 202 is removed from the Instron™ and the radius of the guide section 202 measured using an optical measurement device. The guide section 202 is displaced axially with the ends of the guide wire fixed in rotation. The radius R is recorded at axial displacements $\delta_a$ corresponding to those at which the axial displacement $\delta_a$ and axial force $F_a$ measurements were taken.

Using the experimental setup described above, we can exert an axial force $F_a$ on the guide section 202 over substantially its full range of deflection. For example, when measuring a 1 cm length guide section, use 10–50 discrete deflections. At each deflection, measure and record the axial displacement $\delta_a$, axial force $F_a$ and radius R of the guide section 202. Utilizing this data, $\delta_a$ and $F_a$ can be determined as a function of R.

Figure 6:
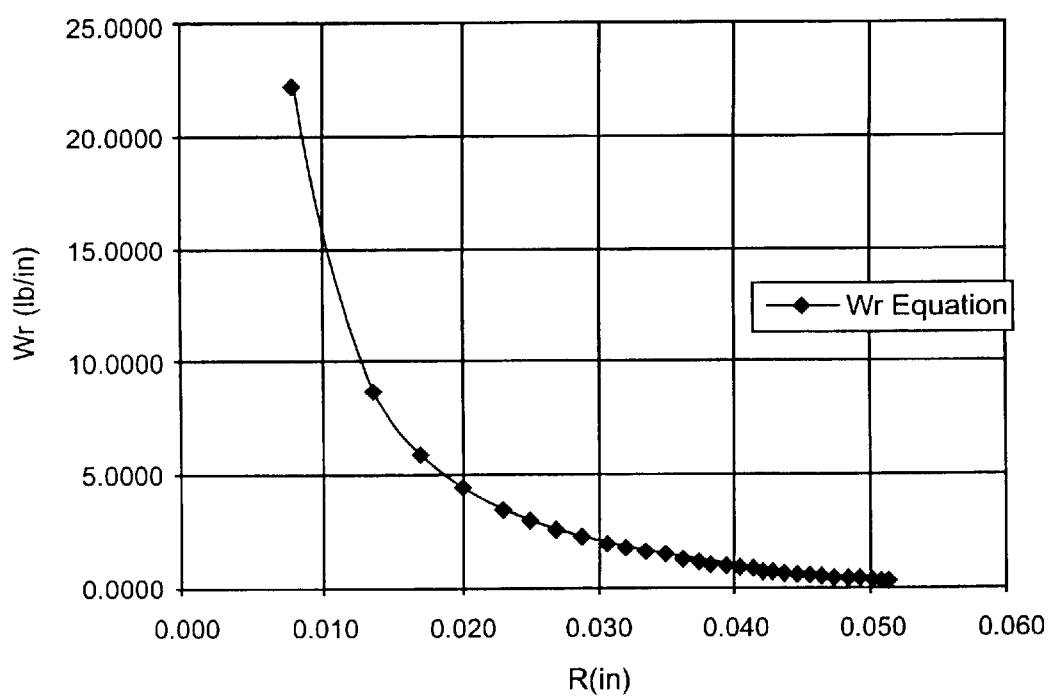
FIG. 6 is a graph of the outward radial force ($W_r$).

Following the determination of the values and relationships described above, calculate and graph $W_r$ as a function of R of the helical guide section. An example of which is shown in FIG. 6.

7. Method of Determining the Force Exerted by a Catheter ($P_{eff}$)

A method of determining the outward radial force $P_{eff}$ a catheter distal tip 402 exerts against a lumen wall 302 while traversing a given helical guide section 202 using the physical and geometric properties of the helical guide section 202 and catheter 400 as defined above and solving the following equation for $P_{eff}$:

$$P_{eff} = (((E_g I_g) F_a \delta_a)/(2 S_{tot} R_k R_o R^2))^{1/2} (L_{eff}) + E_g I_g [((1/R_o) - (1/R))((1/R_o R^2) - (1/R_c R^2))]^{1/2} + ((96 F_a^2 R^2 N)/(d^4 G)) - ((3(E_c I_c) \delta_c)/(L_c^3))$$

The equation for $P_{eff}$ is comprised of four terms: the first three terms are expressions of the outward radial force the helical guide section 202 exerts on the distal end of the catheter 406, the fourth term is the resistive force of the catheter due to its beam stiffness. Subtracting the resistive force of the catheter from the total force exerted outwardly by the helical guide section 202 on the catheter 400 results in the net force of the distal end of the catheter 406 against the lumen wall 302. If $P_{eff}$ is positive the catheter 400 is exerting an outward force on the wall of the lumen 302. If $P_{eff}$ is zero the resistive force of the catheter distal tip 402 is balanced with the outward radial force the helical guide section 202 is exerting on the catheter distal tip 402 and the catheter distal tip 402 is resting on the wall of the lumen 302 but not exerting any force on the wall of the lumen 302. If $P_{eff}$ is negative the resistive force of the catheter exceeds the outward force of the helical guide section 202 on the catheter distal tip 402 and the catheter distal tip 402 is no longer in contact with the wall of the lumen 302.

The modulus of elasticity of the catheter ($E_c$) can be found in published sources. The catheter's moment of inertia ($I_c$) can be calculated from the known geometry of the catheter. If the catheter is a composite, the effective $E_c$ and $I_c$ can be calculated for the composite. The product $E_c I_c$ in the catheter (fourth) term of the equation for $P_{eff}$ can alternately be determined empirically by performing a beam stiffness test on the catheter 400.

When determining the effective length of the catheter in bending ($L_c$) careful consideration must be given to competing factors. In practice, when using a catheter 400 in a body lumen 300, the maximum distance that the catheter can be deflected is determined by the diameter of that lumen 300. The distance the catheter 400 will be deflected in use in a body lumen 300 is estimated to be between 0.5 mm and 5 mm. The specific maximum deflection can be determined by the greatest radius of the largest guide section 202 intended for use with this catheter 400. The effective beam length of the catheter being used in a body lumen 300 varies depending on the body lumen 300 in which the catheter 400 is inserted. In the tortuous anatomy of the coronary arteries the effective beam length of the catheter 400 may be short. However, if the catheter 400 is inserted into a straight lumen, the effective beam length 410 of the catheter 400 will be longer. Here, the effective beam length $L_c$ of the catheter 400 in use is estimated to be between 1 cm and 5 cm.

The intent of the cantilever beam test is to model the effective beam length of the catheter in use. Determining an effective beam length $L_c$ that models the actual use of the catheter can be difficult. The effective beam length $L_c$ of the catheter in the cantilever beam test should best be determined based on its specific usage. Because the stiffness of a beam increases inversely with length, a limit on the minimum length of the catheter used during the cantilever beam test is defined. For definition purposes in the present invention, it will be defined that the minimum effective beam length $L_c$ of the catheter 400 will be that distance that the catheter 400 can be deflected in the largest lumen 300 expected for use from the center axis of the lumen 300 to the lumen wall 302 without permanent deformation to the catheter 400. The maximum deflection distance is defined as the largest radius of the largest guide section 202 intended for use with the catheter 400.

The effective beam length $L_c$ of the catheter 400 for the cantilever beam test will be determined based on competing considerations involved for the specific use of the device. It will be appreciated by those schooled in the art that if the catheter distal tip 406 is a rigid section, the resistance value of the catheter 400 could exceed the outward force of the guide section 202. Should the minimum deflection required above result in permanent deformation to the catheter distal tip 406 during the cantilever beam test, that effective beam length $L_c$ is too short to be a representative model of the catheter 400 in actual use.

To measure the force of the catheter, mount the catheter 400 in an instrument capable of measuring force and deflection (e.g., an Instron™), with the catheter 400 having an effective beam length L discussed above. The catheter 400 must be prepared such that its stiffness will be that seen during its use. Thus if the guide section 202 passes through a lumen in the catheter during use, the guide section 202 must be inserted into the catheter 400 prior to testing in such a way that the guide section 202 contributes to the stiffness of the catheter 400 but does not externally restrict the deflection of the catheter 400. Measure and record the force required to deflect the catheter orthogonal to its major axis from zero deflection (its natural, free state) to a deflection at a minimum equal to the greatest free state radius of the largest guide section 202 intended for use with this catheter 400.

To graph the equation of $P_{eff}$ for all possible R of the helical guide section, there are several possible methods to generate the dependent variables $R_k$, $\delta_a$, $F_a$, $\delta_c$ and $L_{eff}$. Utilizing geometric relationships, $\delta_a$, $R_k$ and $\delta_c$ can be written in terms of the R. $L_{eff}$ can be calculated using the theory of contacting surfaces (e.g., Hertz contact theory) and as such, $L_{eff}$ can be written in terms of R.

Figure 7A:
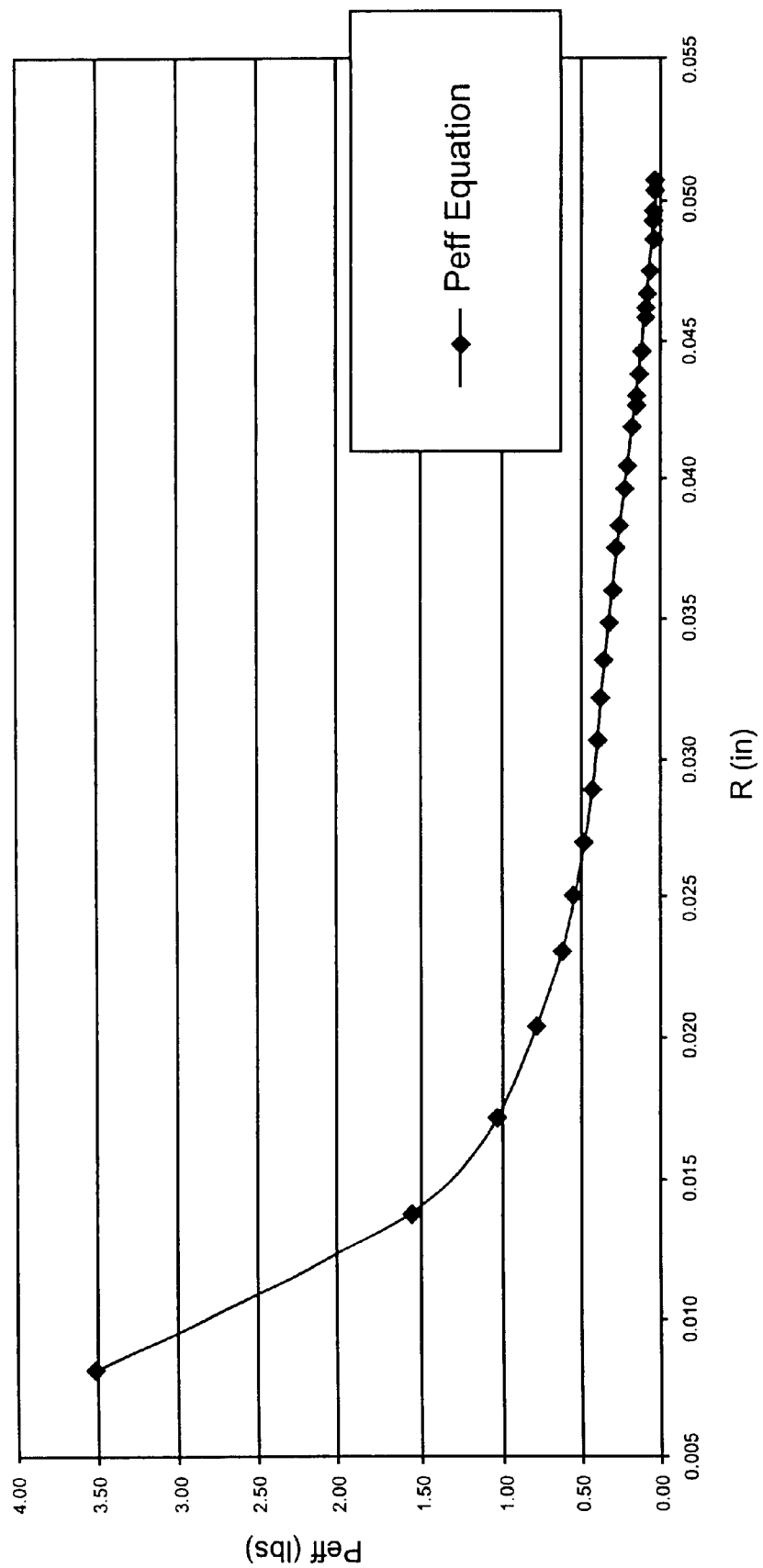
FIGS. 7A and 7B are graphs of the $P_{eff}$ value against radius of the guide section.
Figure 7B:
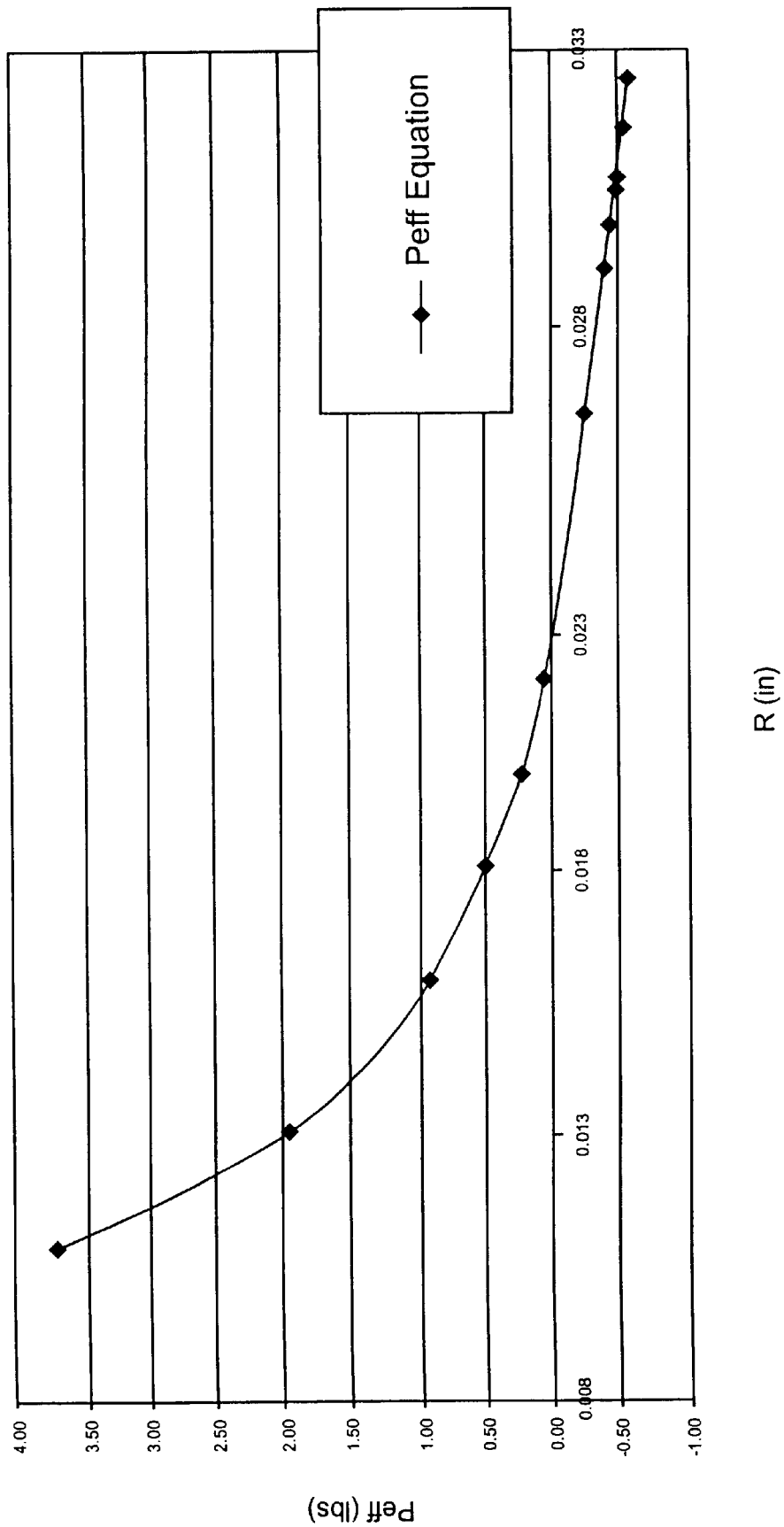

Alternately, $L_{eff}$ can be determined empirically (e.g., deploy the catheter 400 and helical guide section 202 in a plastic tube and measure $L_{eff}$ using polarized light to visualize the contact between the catheter distal end 406 and the tube wall). Following the determination of the values and relationships described above, calculate and graph $P_{eff}$ for all possible values of R. If $P_{eff}$ is zero or positive for all possible values of R (See FIG. 7A), the catheter distal end 406 will remain in contact with the wall of the lumen 302 for all possible values of R. If $P_{eff}$ is negative for any possible value or R (See FIG. 7B), the distal end of the catheter 406 will not be in contact with the lumen wall 302 for any value of R.

The lower limit on R is the radius from the center of the catheter to the outside of the catheter. Because the helical guide section 202 conforms to the lumen 300, a lumen 300 with a radius equal to the radius of the catheter is the smallest lumen in which the catheter will fit. If the lumen radius is smaller than that of the catheter 400, the catheter 400 cannot operate within that lumen 300. As such, the lower limit on R of the helical guide section is the radius of the outside of the catheter. The upper limit on R is the free, unconstrained radius of the helical guide section $R_o$. At $R_o$ the helical guide section 202 is in its free, non-deformed state and as such, the helical guide section 202 is no longer capable of exerting a force against the wall of the lumen 300.

8. Helical Perfusion Wire with a High Radial Force

Figure 8:
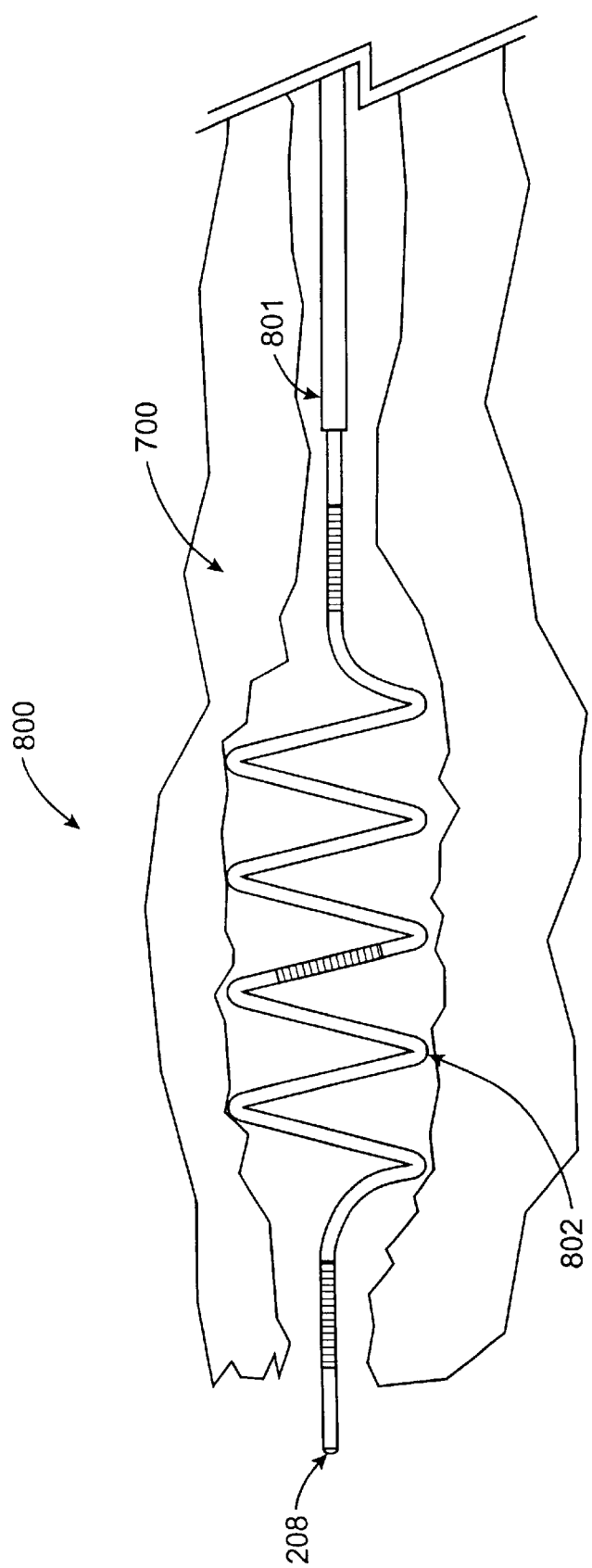
FIG. 8 show various forms of the perfusion wire.

FIG. 8 shows an alternative embodiment of the present invention. The perfusion wire 800 can be made having an outward radial force ($W_r$) in excess of 20 pounds per inch. Many of the features of the perfusion wire are similar to the wire previously described. However the perfusion wire requires a helical support section 802 made of a more robust material than that of the helical guide section 202. The wire cross sections illustrated in FIGS. 5M and 5N provide greater structural integrity and outward radial force ($W_r$) when made of a strong inner material such as stainless steel with a shape memory cladding like nickel-titanium.

The perfusion wire 800 is designed for deployment within a blood vessel 700 that is either diseased and substantially occluded, or has been perforated and collapsed due to loss of local blood pressure. In deployment of the perfusion wire a guide catheter 801 is used to cross the region where the perfusion wire 800 is to be deployed. The guide catheter 801 is then retracted while the perfusion section 802 is deployed. Once free of the constraints of the guide catheter 801, the perfusion section 802 resumes its natural shape. The perfusions section exerts an outward radial force ($W_r$) sufficient to open a passage through a collapsed blood vessel, or substantially occluded blood vessel without danger of damaging the vessel further, or deforming the guide catheter 801.

9. Portable Force Resistance Meter

Figure 9A:
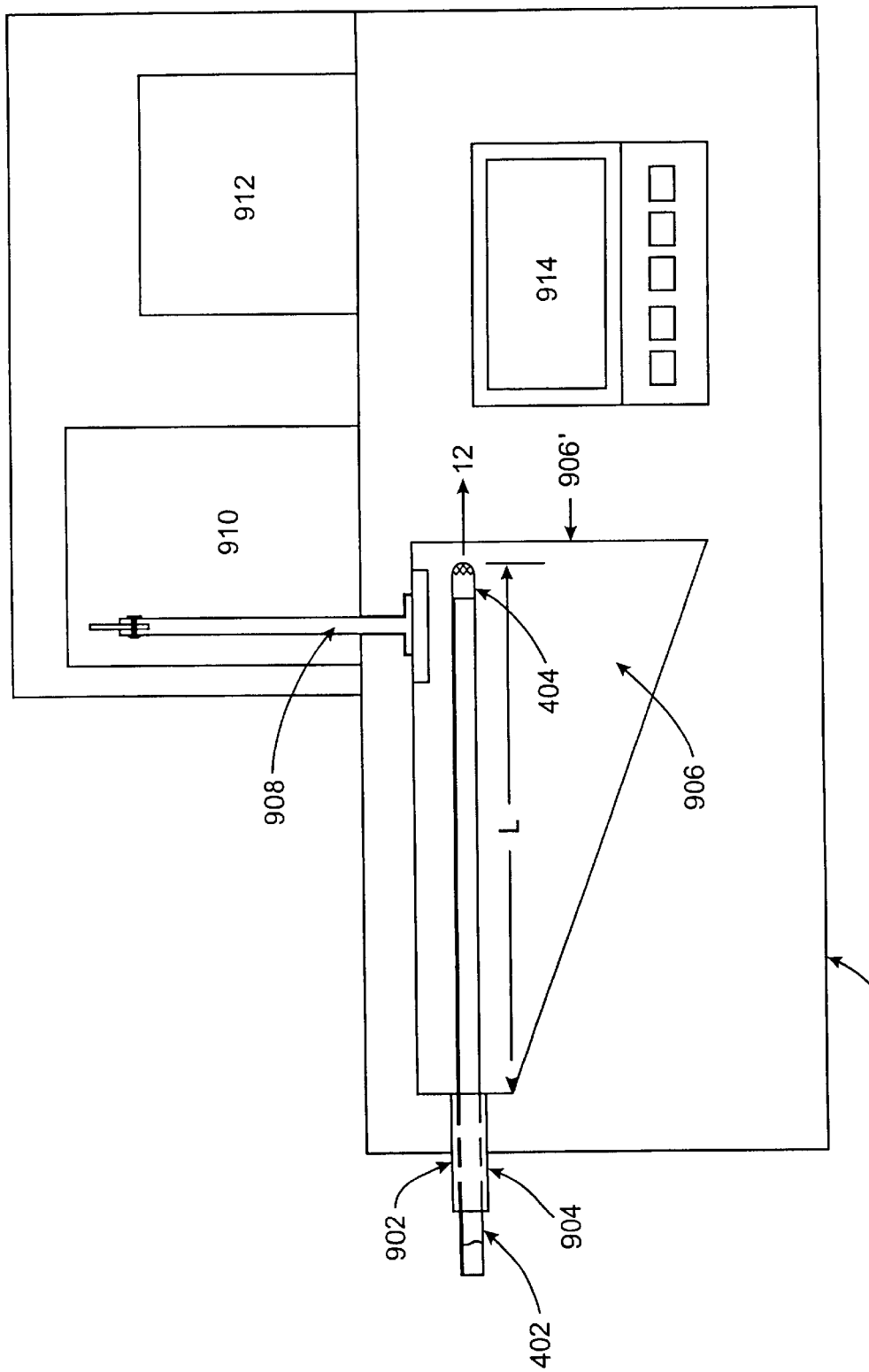
FIGS. 9A and 9B show a portable force resistance meter.
Figure 9B:
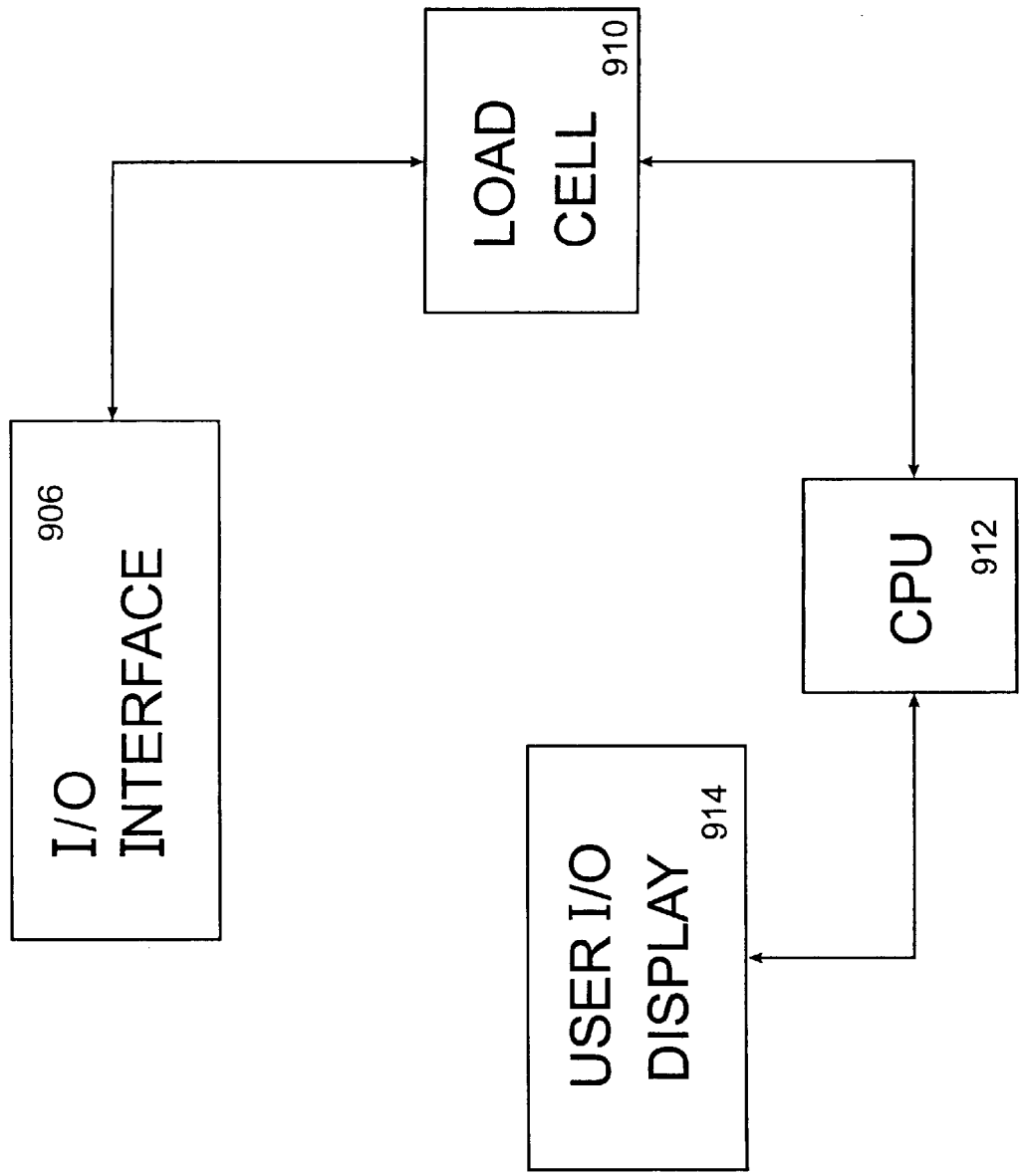

FIGS. 9A and 9B illustrate a portable force measuring unit 900. The force measuring unit 900 of the present invention is used for determining a catheter resistance force value. The preferred embodiment is a small, hand held unit having a port 902 for receiving the distal tip 404 of a catheter 402. The receiving port 902 is generally large enough to receive any catheter 402 ordinarily used in a body lumen with an adaptable entry collar 904 which can be secured around the catheter 402 to lock it in place. The receiving port 902 leads to a test lumen 906 where the catheter distal tip 404 extends into. The catheter distal tip 404 enters at the proximal end 906' of the test lumen 906 and the distal tip 404 extends to the distal end 906' of the test lumen 906. At the distal end 906' of the test lumen 906 a deflection gauge 908 can be used to push the catheter tip 404 a precise distance off the axis 12 of the test lumen 906. A load cell 910 is connected to the deflection gauge 908 to determine the beam stiffness of the catheter 402.

A microprocessor 912 is used to collect and interpret the data collected by the load cell 910 and the test lumen 906. A display unit 914 then indicates the catheter beam stiffness value for use in matching an appropriate guidewire 200 to the catheter 402. FIG. 9B illustrates the electronic element organization of the hand held force meter 900.

While the present invention has been described in the above description, the scope of the present invention is broader than can be reasonably described in a single document as will be come clear to an individual of skill in the art upon review of the present disclosure and the appended claims.

What is claimed is:

1. A guidewire having a generally straight proximal section, and a distal section having a helical support section which defines a curved three dimensional profile that is diametrically larger than the diameter of the proximal section, the helical support section capable of elongation into a substantially straight profile when constrained and expansion to a wider diameter when unconstrained, the helical support section exerting an outward radial force ($W_r$) less than 20 lbs/in when axially extended so the diameter of the helical guide section is half the unconstrained diameter, wherein $W_r$ is determined by the formula:

$$(((SS)F_a\delta_a)/(2S_{tot}R_kR_oR^2))^{1/2}$$

wherein

SS=the measured or calculated beam stiffness of the helical support section;

$S_{tot}$=the measured length of the helical support section;

$\delta_a$=the measured axial extension of the guide section at ½ $R_o$;

$F_a$=the applied axial force to elongate the helical support section by $\delta_a$ with ends of the helical guide section fixed in rotation;

R=the measured average radius of the helical support section when constrained;

$R_k$=the average measure of R less half the wire diameter; and $R_o$=the measured average radius of the helical support section when unconstrained.

2. The guidewire of claim 1, wherein the shape memory alloy is nickel-titanium.

3. The guidewire of claim 1, wherein the helical support section is between 0.01" and 1.0" in diameter.

4. The guidewire of claim 1, wherein the helical support section is between 0.04" and 0.24" in diameter.

5. The guidewire of claim 1, wherein the helical support section is between 0.08" and 0.2" in diameter.

6. The guidewire of claim 1 wherein the helical support section has a pitch between 0.01" and 0.48."

7. The guidewire of claim 1 wherein the helical support section has a pitch between 0.04" and 0.31."

8. The guidewire of claim 1, wherein the helical support section has a pitch between 0.08" and 0.24."

9. The guidewire of claim 1, wherein the helical support section exerts an outward radial force between 0.001 and 3 lbs/in.

10. The guidewire of claim 1, wherein the helical support section exerts an outward radial force between 0.01 and 1 lb/in.

11. The guidewire of claim 1 further comprising at least one radiopaque marker.

12. The guidewire of claim 1 further comprising an atraumatic tip.

13. The guidewire of claim 1, wherein the $S_{tot}$ of the helical support section is 0.2" to 5.0."

14. The guidewire of claim 1, wherein the $S_{tot}$ of the helical support section is between 1.5" and 3.5."

15. A perfusion wire having a generally straight proximal section, and a distal section having a helical perfusion section having ends and which defines a curved three dimensional profile that is diametrically larger than the diameter of the proximal section, the helical perfusion section being capable of elongation into a substantially straight profile when constrained and expansion to a wider diameter when relaxed, the helical perfusion section exerting an outward radial force ($W_r$) greater than 10 lbs/in when axially extended with the helical perfusion section ends fixed in rotation, until the helical perfusion section is at one half the unconstrained perfusion guide section radius, wherein $W_r$ is determined by the formula:

$$(((PS)F_a\delta_a)/(2S_{tot}R_kR_oR^2))^{1/2}$$

wherein

PS=the measured or calculated beam stiffness of the helical perfusion section;

$S_{tot}$=the measured length of the helical perfusion section;

$\delta_a$=the measured axial extension of the helical perfusion section at ½ $R_o$;

$F_a$=the applied axial force to elongate the helical perfusion section by $\delta_a$;

$R_k$=the average measure of R less half the wire diameter;

$R_o$=the measured average radius of the helical perfusion section when unconstrained;

R=the measure average radius of the helical perfusion section when constrained.

16. The perfusion of claim 15, wherein the shape memory alloy is nickel-titanium.

17. The perfusion wire of claim 15, wherein the shape memory alloy is a two way thermally sensitive shape memory alloy having a transition temperature below 32° Celsius.

18. The perfusion of claim 15, wherein the helical support section is between 0.01" and 1.0" in diameter.

19. The perfusion of claim 15, wherein the helical support section is between 0.04" and 0.24" in diameter.

20. The perfusion of claim 15, wherein the helical support section is between 0.08" and 0.20" in diameter.

21. The perfusion of claim 15, wherein the helical support section has a pitch between 0.02" and 0.48."

22. The perfusion of claim 15, wherein the helical support section has a pitch between 0.04" and 0.31."

23. The perfusion of claim 15, wherein the helical support section has a pitch between 0.08" and 0.24."

24. The perfusion of claim 15, further comprising at least one radiopaque marker.

25. The perfusion of claim 15, further comprising an atraumatic tip.

26. The perfusion of claim 15, wherein the Stot of the helical support section is 0.2" to 5.0."

27. The perfusion of claim 15, wherein the Stot of the helical support section is between 1.5" and 3.5."

28. A system comprising:

a guidewire having a straight proximal section and a distal section, the distal section having a helical guide section capable of changing geometry when constrained in a lumen varying between a substantially straight profile to a fully relaxed profile and exerting an outward radial force on a body lumen less than 15 lbs/in when the radius of the constrained guide section is eighty percent (0.8) of the unconstrained guide section radius; and a catheter capable of tracking over said guidewire wherein and the catheter is capable of following the helical guide section while remaining in contact with a lumen surface, the catheter exerting an outward radial force on the lumen at substantially the point of entry for the guidewire wherein the catheter exerts an outward radial force on the lumen less than 4 lbs/inch.

29. The helical guide section of claim 28 wherein the force the catheter exerts on the lumen ($P_{eff}$) is determined by the formula:

$$(((GS)F_a\delta_a)/(2S_{tot}R_kR_oR^2))^{1/2}(L_{eff})+E_gI_g[((1/R_o)-(1/R))((1/R_oR^2)-(1/R_cR^2))]^{1/2}+((96F_a^2R^2N)/(d^4G))-((3(CS)\delta_c)/(L_c^3))$$

wherein

GS=the measured or calculated beam stiffness of the helical guide section;

$S_{tot}$=the measured length of the helical guide section;

$\delta_a$=the measured axial extension of the helical perfusion section at ½ $R_o$;

$F_a$=the applied axial force to elongate the helical guide section by $\delta_a$;

$R_k$=the average measure of R less half the wire diameter;

$R_o$=the measured average radius of the helical guide section when unconstrained;

R=the measure average radius of the helical guide section when constrained;

$R_c$=the average diameter of the catheter tracking over the helical guide section;

$L_{eff}$=the effective length of contact between the distal section of the catheter and the luminal wall;

N=the number of coils in the helical guide section;

d=the average wire diameter of the helical guide section;

G=the shear modulus of elasticity of the helical guide section;

CS=the measured or calculated beam stiffness of the catheter;

$\delta_c$=End displacement of the catheter; and $L_c$=the average length of the catheter in the bending test for (CS).

30. The guidewire of claim 29, wherein the Stot of the helical support section is 0.2" to 5.0."

31. The guidewire of claim 29, wherein the Stot of the helical support section is between 1.5" and 3.5."

32. The guidewire as described in claim 28 being made of a shape memory alloy.

33. The guidewire of claim 32, wherein the shape memory alloy is nickel-titanium.

34. The guidewire of claim 28, wherein the helical support section is between 0.01" and 1.0" in diameter.

35. The guidewire of claim 28, wherein the helical support section is between 0.04" and 0.24" in diameter.

36. The guidewire of claim 28, wherein the helical support section is support section is between 0.08" and 0.20" in diameter.

37. The guidewire of claim 28, wherein the helical support section has a pitch between 0.02" and 0.48."

38. The guidewire of claim 28, wherein the helical support section has a pitch between 0.04" and 0.31."

39. The guidewire of claim 28 wherein the helical support section has a pitch preferably between 0.08" and 0.24."

40. The guidewire of claim 28, wherein the outward radial force the catheter exerts ($P_{eff}$) is between 0.0001 and 2 lbs/in.

41. The guidewire of claim 28, wherein the outward radial force the catheter exerts ($P_{eff}$) is between 0.001 and 1 lb/in.

42. The guidewire of claim 28, wherein the outward radial force the catheter exerts ($P_{eff}$) is less than 2 lbs/in.

43. The guidewire of claim 28 further comprising at least one radiopaque marker.

44. The guidewire of claim 28 further comprising an atraumatic tip.

45. The system described in claim 28, wherein the catheter comprises an ultrasonic device.

46. The medical device of claim 28, wherein the catheter has a rotational torque member.

47. The system described in claim 28, wherein the catheter is a diagnostic device.

48. The catheter as in claim 47, wherein the diagnostic device is capable of producing images.

\* \* \* \* \*